US006943340B2

(12) United States Patent
Tubel et al.

(10) Patent No.: US 6,943,340 B2
(45) Date of Patent: Sep. 13, 2005

(54) METHOD AND APPARATUS OF PROVIDING AN OPTICAL FIBER ALONG A POWER SUPPLY LINE

(75) Inventors: Paulo S. Tubel, The Woodlands, TX (US); Glynn Williams, Andover (GB); Kurt A. Hickey, Humbie, TX (US); Nigel Leggett, Andover (GB)

(73) Assignee: Sensor Highway Limited, Southampton (GB)

( * ) Notice: Subject to any disclaimer, the term of this patent is extended or adjusted under 35 U.S.C. 154(b) by 0 days.

(21) Appl. No.: 10/884,057

(22) Filed: Jul. 2, 2004

(65) Prior Publication Data

US 2004/0256100 A1 Dec. 23, 2004

Related U.S. Application Data

(62) Division of application No. 10/336,154, filed on Jan. 3, 2003, now Pat. No. 6,828,547, which is a division of application No. 09/778,696, filed on Feb. 6, 2001, now Pat. No. 6,531,694, which is a division of application No. 09/071,764, filed on May 1, 1998, now Pat. No. 6,281,489.
(60) Provisional application No. 60/079,446, filed on Mar. 26, 1998, provisional application No. 60/073,425, filed on Feb. 2, 1998, provisional application No. 60/062,953, filed on Oct. 10, 1997, provisional application No. 60/052,042, filed on Jul. 9, 1997, provisional application No. 60/048,989, filed on Jun. 9, 1997, and provisional application No. 60/045,354, filed on May 2, 1997.

(51) Int. Cl.[7] .............................. E21B 41/00; G01J 5/08
(52) U.S. Cl. ................ 250/227.14; 385/12; 166/250.01
(58) Field of Search ................ 250/227.14; 166/250.01, 166/62, 252.1; 385/10, 12, 13, 15, 37, 38

(56) References Cited

U.S. PATENT DOCUMENTS 4,162,400 A   7/1979   Pitts, Jr.

(Continued)

FOREIGN PATENT DOCUMENTS

| EP | 0175298 | 3/1986 |
|----|---------|--------|
| EP | 0466155 | 1/1992 |
| EP | 0677748 | 10/1995 |
| GB | 2165062 | 4/1986 |
| RU | 2124256 | 12/1998 |
| WO | WO 96/24747 | 8/1996 |
| WO | WO 96/24749 | 8/1996 |

OTHER PUBLICATIONS

Karaman O. S. et al., "A Field Trial to Test Fiber Optic Sensors for Downhole Temperature and Pressure Measurements, West Coalings Field, California", *Offshore Europe Proceedings*, May 22, 1996, pp. 351–357.

Pigeon F. et al., "A Vibration Sensor, Using Telecommunication Grade Monomode Fiber, Immune to Temperature Variations", *Journal De Physique III, Editions De Physique*, Paris, France, vol. 3, No. 9, Sep. 1, 1993, pp. 1835–1838.

(Continued)

*Primary Examiner*—Stephone B. Allen
(74) *Attorney, Agent, or Firm*—Wayne I. Kanak; Dan C. Hu

(57) ABSTRACT

This invention provides a method for controlling production operations using fiber optic devices. An optical fiber carrying fiber-optic sensors is deployed downhole to provide information about downhole conditions. Parameters related to the chemicals being used for surface treatments are measured in real time and on-line, and these measured parameters are used to control the dosage of chemicals into the surface treatment system. The information is also used to control downhole devices that may be a packer, choke, sliding sleeve, perforation device, flow control valve, completion device, an anchor or any other device. Provision is also made for control of secondary recovery operations online using the downhole sensors to monitor the reservoir conditions. The present invention also provides a method of generating motive power in a wellbore utilizing optical energy. This can be done directly or indirectly, e.g., by first producing electrical energy that is then converted to another form of energy.

14 Claims, 19 Drawing Sheets

U.S. PATENT DOCUMENTS

| | | |
|---|---|---|
| 4,637,071 A | 1/1987 | Jones et al. |
| 4,976,789 A | 12/1990 | Holloman et al. |
| 5,043,573 A | 8/1991 | Banks |
| 5,285,204 A | 2/1994 | Sas-Jaworsky |
| 5,363,095 A | 11/1994 | Normann et al. |
| 5,499,313 A | 3/1996 | Kleinerman |
| 5,892,860 A * | 4/1999 | Maron et al. .................. 385/12 |

OTHER PUBLICATIONS

Botto G. et al., "Electronic, Fiber–Optic Technology: Future Options for Permanent Reservoir Monitoring", *Offshore Europe Proceedings*, Sep. 25, 1994, pp. 215–224.

Heatth S.M. et al., "On–Line Chemical Sensing Technology for Downhole and Topside Monitoring of Produced Brines", *Advances in Solving Oilfield Scaling Conference*, Nov. 20, 1995, pp. 1–19.

* cited by examiner

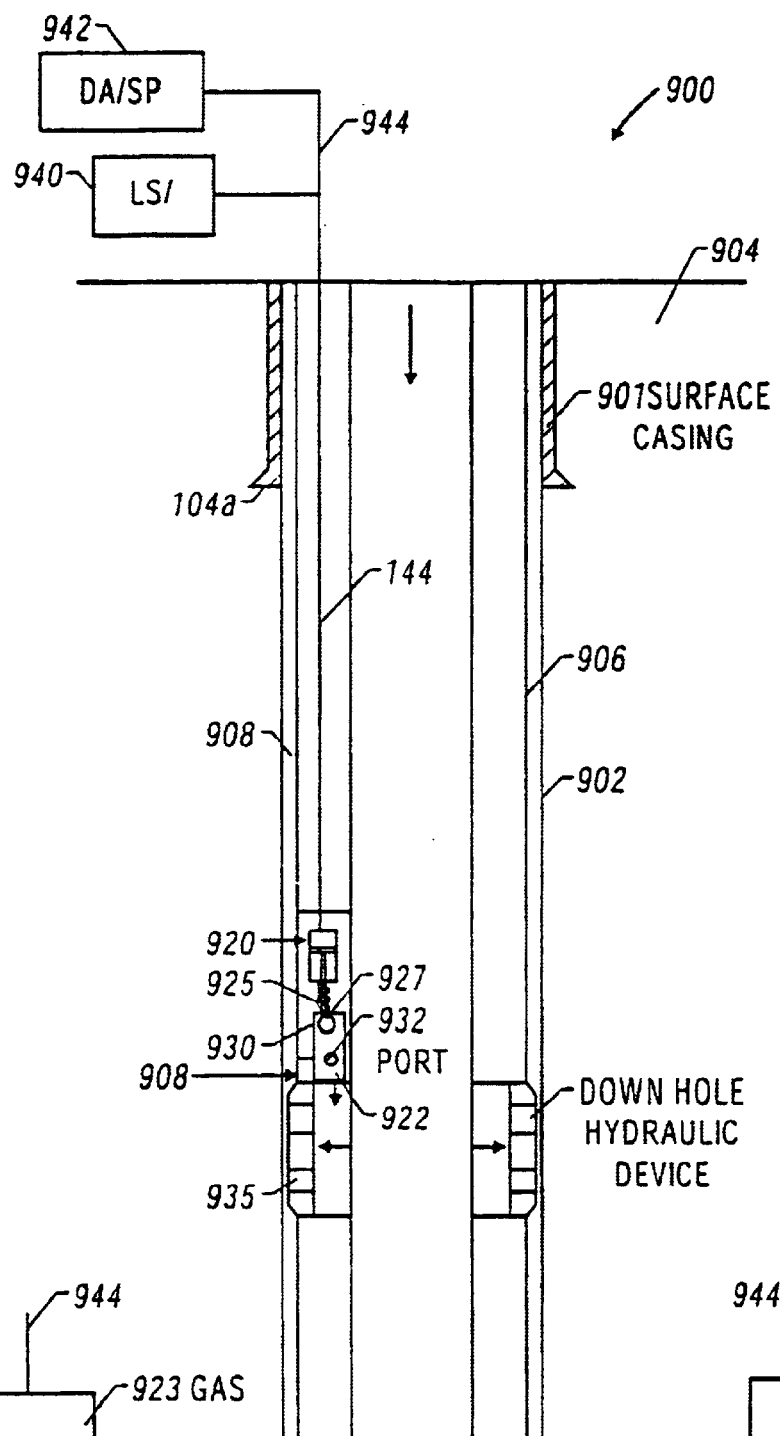
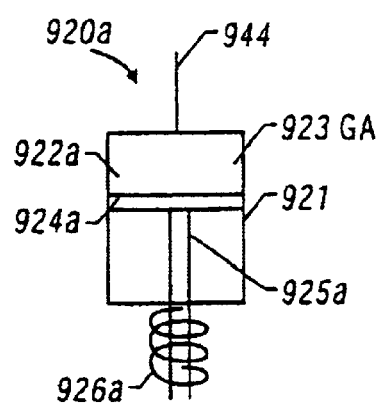
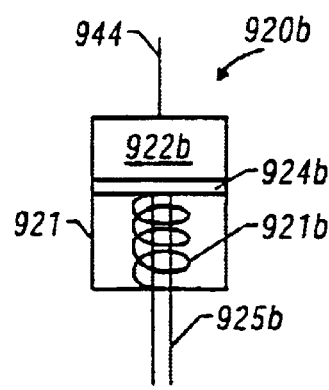
FIGURE 15
FIGURE 15A
FIGURE 15B

METHOD AND APPARATUS OF PROVIDING AN OPTICAL FIBER ALONG A POWER SUPPLY LINE

CROSS REFERENCE TO RELATED APPLICATIONS

This is a divisional of U.S. Ser. No. 10/336,154, filed Jan. 3, 2003, now U.S. Pat. No. 6,828,547, which is a divisional of U.S. Ser. No. 09/778,696, filed Feb. 6, 2001, now U.S. Pat. No. 6,531,694, which is a divisional of U.S. Ser. No. 09/071,764, filed May 1, 1998 (now U.S. Pat. No. 6,281,489), which claims the benefit under 35 U.S.C. § 119(e) of Provisional U.S. Patent Applications Ser. Nos. 60/045,354 filed on May 2, 1997; 60/048,989 filed on Jun. 9, 1997; 60/052,042 filed on Jul. 9, 1997; 60/062,953 filed on Oct. 10, 1997; 60/073,425 filed on Feb. 2, 1998; and 60/079,446 filed on Mar. 26, 1998. Each of the reference applications is hereby incorporated by reference.

BACKGROUND OF THE INVENTION

1. Field of the Invention

This invention relates generally to oilfield operations and more particularly to the downhole apparatus utilizing fiber optic sensors and use of same in monitoring the condition of downhole equipment, monitoring certain geological conditions, reservoir monitoring and remedial operations.

2. Background of the Art

A variety of techniques have been utilized for monitoring wellbores during completion and production of wellbores, reservoir conditions, quantities of hydrocarbons (oil and gas), operating downhole devices in the wellbores, and determining the physical condition of the wellbore and downhole devices.

Reservoir monitoring typically involves determining certain downhole parameters in producing wellbores at various locations in one or more producing wellbores in a field, typically over extended time periods. Wireline tools are most commonly utilized to obtain such measurements, which involves transporting the wireline tools to the wellsite, conveying the tools into the wellbores, shutting down the production and making measurements over extended periods of time and processing the resultant data at the surface. Seismic methods wherein a plurality of sensors are place on the earth's surface and a source placed at the surface or downhole are utilized to provide maps of subsurface structure. Such information is used to update prior seismic maps to monitor the reservoir of field conditions. Updating excision 3-D seismic maps over time is referred to in industry as "4-D Seismic". The above described methods are very expensive. The wire methods are utilized at relatively large time intervals, thereby not providing continuous information about the wellbore condition or that of the surrounding formations.

Placement of permanent sensors in the wellbore, such as temperature sensors, pressure sensors, accelerometers and hydrophones has been proposed to obtain continuous wellbore and formation information. A separate sensor is utilized for each type of parameter to be determined. To obtain such measurements from the entire useful segments of each wellbore, which may have multi-lateral wellbores, requires using a large number of sensors, which requires a large amount of power, data acquisition equipment and relatively large space in the wellbore: this may be impractical or prohibitively expensive.

Once the information has been obtained, it is desirable to manipulate downhole devices such as completion and production strings. Prior art methods for performing such functions rely on the use of electrically operated devices with signals for their operation communicated through electrical cables. Because of the harsh operating conditions downhole, electrical cables are subject to degradation. In addition, due to long electrical path lengths for downhole devices, cable resistance becomes significant unless large cables are used. This is difficult to do within the limited space available in production strings. In addition, due to the high resistance, power requirements also became large.

One particular arrangement in which operation of numerous downhole devices becomes necessary is in secondary recovery. Injection wells have, of course, been employed for many years in order to flush residual oil in a on toward a production well and increase yield from the area. A common injection scenario is to pump steam down an injection well and into the formation which functions both to heat the oil in the formation and force its movement through the practice of steam flooding. In some cases, heating is not necessary as the residual oil is in a flowable form, however in some situations the oil is in such a viscous form that it requires heating in order to flow. Thus, by using steam one accomplishes both objectives of the injection well: 1) to force residual oil toward the production well and 2) to heat any highly viscous oil deposits in order mobilize such oil to flow ahead of the flood front toward the production well. As is well known to the are, one of the most common drawbacks of employing the method above noted with respect to injection wells is an occurrence commonly identified as "breakthrough". Breakthrough occurs when a portion of the flood front reaches the production well. As happens the flood water remaining in the reservoir will generally tend to travel the path of least resistance and will follow the breakthrough channel to the production well. At this point, movement of the viscous oil ends. Precisely when and where the breakthrough will occur depends upon water/oil mobility ratio, the lithology, the porosity and permeability of the formation as well as the depth thereof. Moreover, other geologic conditions such as faults and unconformities also affect the in-situ sweep efficiency.

While careful examination of the formation by skilled geologists can yield a reasonable understanding of the characteristics thereof and therefore deduce a plausible scenario of the way the flood front will move, it has hot heretofore been known to monitor precisely the location of the flood front as a whole or as individual sections thereof. By so monitoring the flood front, it is possible to direct greater or lesser flow to different areas in the reservoir, as desired, by adjustment of the volume and location of both injection and production, hence controlling overall sweep efficiency. By careful control of the flood front, it can be maintained in a controlled, non fingered profile. By avoiding premature breakthrough the flooding operation is effective for more of the total formation volume, and thus efficiency in the production of oil improved.

In production wells, chemicals are often injected downhole to treat the producing fluids. However, it can be difficult to monitor and control such chemical injection in real time. Similarly, chemicals are typically used at the surface to treat the produced hydrocarbons (i.e., to break down emulsions) and to inhibit corrosion. However, it can be difficult to monitor and control such treatment in real time.

The present invention addresses to above-described deficiencies of the prior art and provides apparatus and methods which utilize sensors (such as fiber optic sensors), wherein each sensor can provide information about more than one parameter to perform a variety of functions. The sensors are used to measure parameters related to the chemical introduction in real time so that the chemical treatment system can be accurately monitored and controlled.

The present invention addresses the above-described deficiencies of prior art and provides apparatus and methods which utilize fiber optic sensors, wherein each sensor can provide information about more than one parameter to perform a variety of functions The sensors may be placed along any length of the wellbore. Sensor segments, each containing one or more sensors, may be coupled to form an active section that may be disposed in the casing or continuous monitoring of the wellbore. Sensors may be distributed in a wellbore or multiple wellbores for determining parameters of interest. Hermetically ad optical fibers coated with high temperature resistant materials are commercially available. Single or multi-mode sensors be fabricated along the length of such optical fibers. Such sensors include temperature, pressure and vibration sensors. Such sensors cam withstand high temperatures in excess of 250 degree Celsius for extended time periods and thus have been found to be useful in wellbore applications. An optical fiber is a special case of an optical waveguide and in most applications, other types of optical waveguides, including those containing a fluid, can usually be substituted for optical fiber.

The present invention provides certain completion and production strings that utilize fiber optical waveguide based sensor and devices. The invention also provides a method of generating electrical power downhole, utilizing light cells installed in the wellbore.

SUMMARY OF THE INVENTION

This invention uses fiber optic sensors to make measurements of downhole conditions in a producing borehole. The measurements include temperature and pressure measurements; flow measurements related to the presence of solids and of corrosion, scale and paraffin buildup; measurements of fluid levels; displacement; vibration; rotation; acceleration; velocity; chemical species; radiation; pH values; humidity, density; and of electromagnetic and acoustic wavefields. These measurements are used for activating a hydraulically-operated device downhole and deploying a fiber optic sensor line utilizing a common fluid conduit. A return hydraulic conduit is placed along the length of a completion string. The hydraulic conduit is coupled to the hydraulically-operated device in a manner such that when fluid under pressure is supplied to the conduit, it would acetate the device. The string is placed or conveyed in the wellbore. Fiber optic cable carrying a number of sensors is forced into one end of the conduit until it returns at the surface at the other end. Light source and signal processing equipment is installed at the surface. The fluid is supplied under sufficient pressure to activate the device when desired. The hydraulically-operated device may be a packer, choke, sliding sleeve, perforating device, flow control valve, completion device, an anchor or any other device. The fiber optic sensors carried by the cable may include pressure sensors, temperature sensors, vibration sensors, and flow measurement sensors.

This invention also provides a method of controlling production from a wellbore. A production string carrying an electrical submersible pump is preferably made at the surface. An optical fiber carrying a plurality of fiber optic sensors is placed along a high voltage line that supplies power to the pump for taking measurements along the wellbore length. In one configuration, a portion of the fiber carrying selected sensors is deployed below the pump. Such sensors may include a temperature sensor, a pressure sensor and a flow rate measurement sensor. These sensors effectively replace the instrumentation package usually installed for the pump.

In an application to control of injection wells, the invention provides significantly more information to well operators thus enhancing oil recovery to a degree not heretofore known. This is accomplished by providing real time information about the formation itself and the flood front by providing permanent downhole sensors capable of sensing changes in the swept and unswept formation and/or the progression of the flood front. Preferably a plurality of sensors would be employed to provide information about discrete portions of strata surrounding the injection well. This provides a more detailed data set regarding the well(s) and surrounding conditions. The sensors are, preferably, connected to a processor either downhole or at the surface for processing of information. Moreover, in a preferred embodiment the sensors are connected to computer processors which are also connected to sensors in a production well (which are similar to those disclosed in U.S. Pat. No. 5,597,042 which is fully incorporated herein by reference) to allow the production well to "talk" directly to the related injection well(s) to provide an extremely efficient real time operation. Sensors employed will be to sense temperature, pressure, flow rate, electrical and acoustic conductivity, density and to detect various light transmission and reflection phenomena. All of these sensor types are available commercially in various ranges and sensitivities which are selectable by one of ordinary skill in the art depending upon particular conditions known to exist in a particular well operation. Specific pressure measurements will also include pressure(s) at the exit valve(s) down the injection well and at the pump which may be located downhole or at the surface. Measuring said pressure at key locations such as at the outlet, upstream of the valve(s) near the pump will provide on about the speed, volume, direction, etc. at/in which the waterflood front (or other fluid) is moving. Large differences in the pressure from higher to lower over a short period of time could indicate a breakthrough. Conversely, pressure from lower to higher over short periods of time could indicate that the flood front had hit a barrier. These conditions are, of course, familiar to one of skill in the art but heretofore far less would have been known since no workable system for measuring the parameters existed. Therefore the present invention since it increases knowledge, increases productivity.

Referring now to the measurement of density as noted above, the present invention uses fluid densities to monitor the flood front the trailing end. As will be appreciated from the detailed discussion herein, the interface between the flood front and the hydrocarbon fluid provides an acoustic barrier from which a signal can be reflected. Thus by generating acoustic signals and mapping the reflection, the profile of the front is generated in 4D i.e., three dimensions over time.

The distributed sensors of this invention find particular utility in the monitoring and control of various chemicals which are injected to the well. Such chemicals are needed downhole to address a large number of known problems such as for scale inhibition and various pretreatment of the fluid being produced. In accordance with the present invention, a chemical injection monitoring and control system includes the placement of one or more sensors downhole in the producing zone for measuring the chemical properties of the produced fluid as well as for measuring other downhole parameters of interest. These sensors are preferably fiber optic based and are formed from a sol gel matrix and provide a high temperature, reliable and relatively inexpensive indicator of the desired chemical parameter. The downhole chemical sensors may be associated with a network of distributed fiber optic sensors positioned along the wellbore for measuring pressure, temperature and/or flow. Surface and/or downhole controllers receive input from the several downhole sensors, and in response thereto, control the injection of chemicals into the borehole.

In still another feature of this invention, parameters related to the chemical being used for surface treatments are measured in real time an on-line, and these measured parameters are used to control the dosage of chemicals into the surface Another aspect of the present invention provides a fiber optic device (light actuated transducer) for generating mechanical energy and methods of using such energy at the well site. The device contains a fluid that rapidly expands in an enclosure upon the application of optical energy. The expansion of the fluid moves a piston in the enclosure. The fluid contracts and the piston is pushed back to its original position by a force device such as spring. The process is then repeated to generate reciprocating motion of a member attached to the piston. The device is like an internal combustion engine wherein the fuel is a fluid in a sealed chamber that expands rapidly when high energy light such as laser energy is applied to the fluid. The energy generated by the optical device is utilized to operate a device in the wellbore. The downhole device may be any suitable device, including a valve, fluid control device, packer, sliding sleeve, safety valve, and an anchor. The motion energy generated by the fiber optic devices may be used to operate a generator to generate electrical power downhole which power is utilized to charge batteries downhole or to directly operate a downhole device and/or provide power to sensors in the wellbore. A plurality of such fiber optic devices may be utilized to increase the energy generated. The devices may also be used as a pump to control the supply of fluids and chemicals in the wellbore.

Examples of the more important of the invention have been summarized rather broadly in order that the detailed description thereof that follows may be better understood, and in order that the contributions the art may be appreciated. There are, of course additional features of the invention that will be described hereinafter and which will form the subject of the claims appended hereto.

BRIEF DESCRIPTION OF THE DRAWINGS

For a detailed understanding of the present invention, reference should be made to the following detailed description of the preferred embodiment, taken in conjunction with the accompanying drawings, in which like elements have been given like numerals, wherein:

FIGS. 15A–15C show the power section of fiber optic devices for use in the system of FIG. 1.

DETAILED DESCRIPTION OF PREFERRED EMBODIMENTS

The various concepts of the present invention will be described in reference to FIGS. 1–17, which show a schematic illustration of wellbores utilizing fiber optic-based sensor and operating devices.

Figure 1:
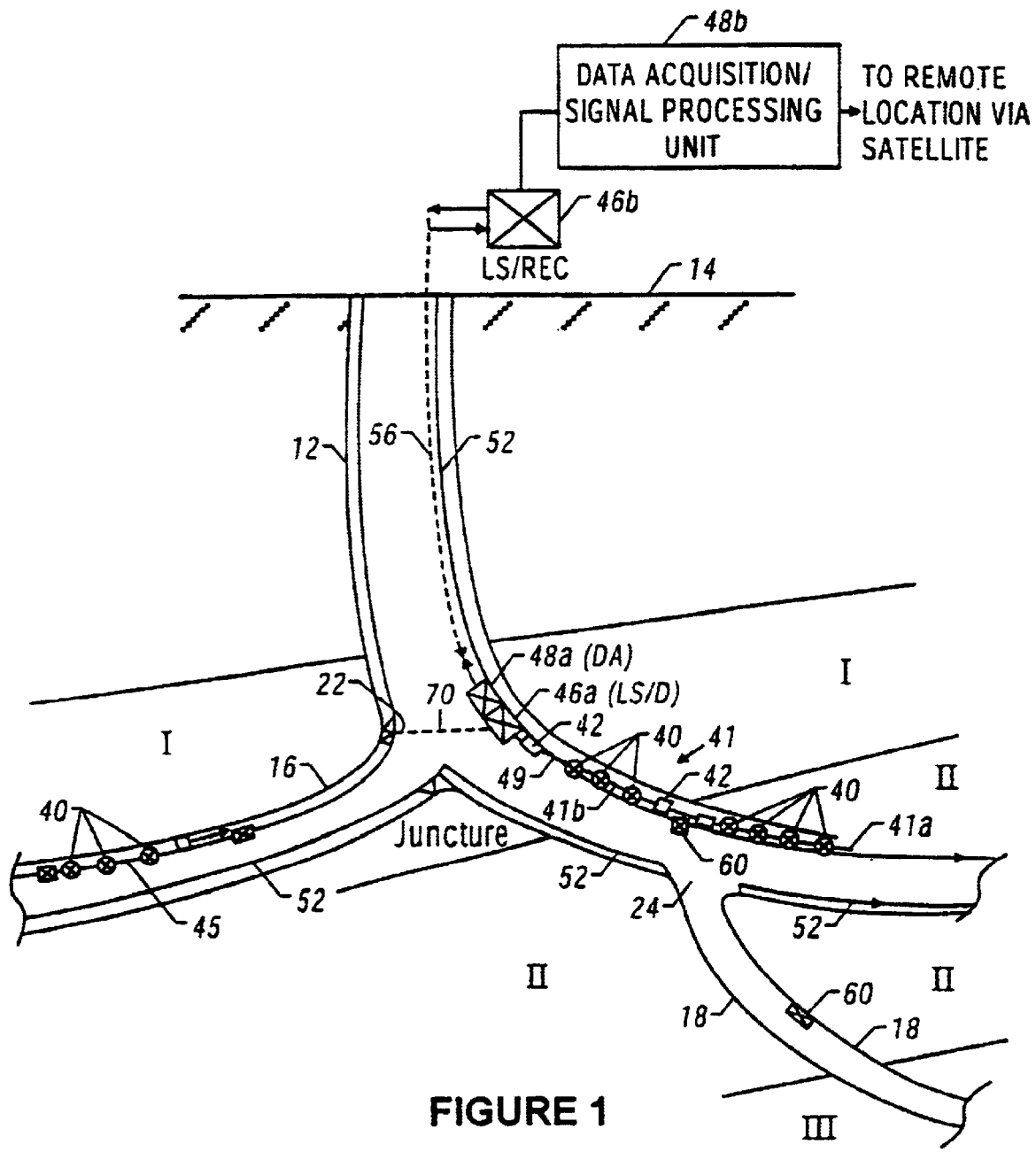
FIG. 1 shows a schematic illustration of an elevational view of a multi-lateral wellbore and placement of fiber optic sensors therein.

FIG. 1 shows an exemplary main or primary wellbore 12 formed from the earth surface 14 and lateral wellbores 16 and 18 formed from the main wellbore 18. For the purpose of explanation, and not as any limitation, the main wellbore 18 is partially formed in a producing formation or pay zone I and partially in a non-producing formation or dry formation II. The lateral wellbore 16 extends from the main wellbore at a juncture 22 into the producing formation I, while the lateral wellbore 16 extents from the main wellbore 12 at juncture 24 into a second producing formation III. For the purposes of this illustration only, the wellbores herein are shown as being drilled on land; however, this invention is equally applicable to offshore wellbores. It should be noted that all wellbore configurations shown and described herein are to illustrate the present invention and are not be construed to limit the inventions claimed herein.

In one application, a number of fiber optic sensors 40 are placed in the wellbore 12. A single or a plurality of fiber optic strings or segments, each such segment containing a plurality of spaced apart fiber optic sensors 40 may be used to install the desired number of fiber optic sensors 40 in the wellbore 12. As an example, FIG. 1 shows two serially coupled segments 41a and 41b, each containing a plurality of spaced apart fiber optic sensors 40. A light source and detector (LS/D) 46a coupled to an end 49 of segment 41a is disposed in the wellbore 12 to transmit light energy to sensors 40 and to receive signals from the sensors 40. A data acquisition unit (DA) 48a is disposed downhole to control the operation of the sensors 40, process downhole sensor signals and data, and to communicate with other equipment and devices, including devices in the wellbores or at the surface shown below in FIGS 2–17.

Alternatively, a light source 46b and the data acquisition and processing unit 48b may be placed on the surface 14. Similarly, fiber optic sensor strings 45 may be disposed in other wellbores in the system, such as wellbores 16 and wellbore 18. A single light source, such as light source 46a or 46b may be used for all fiber optic sensors in the various wellbores, such as shown by the dotted line 70. Alternatively, multiple sources and data acquisition units may be used downhole, at the surface, or in combination. Since the same sensor may make different types of measurements, the data acquisition unit 48a or 48b is programmed to multiplex the measurements. Multiplexing techniques are well known in the art and are thus not described in detail herein. The data acquisition unit 46a may be programmed to control the downhole sensors autonomously or upon receiving command signals from the surface or a combination of these methods.

Figure 1A:
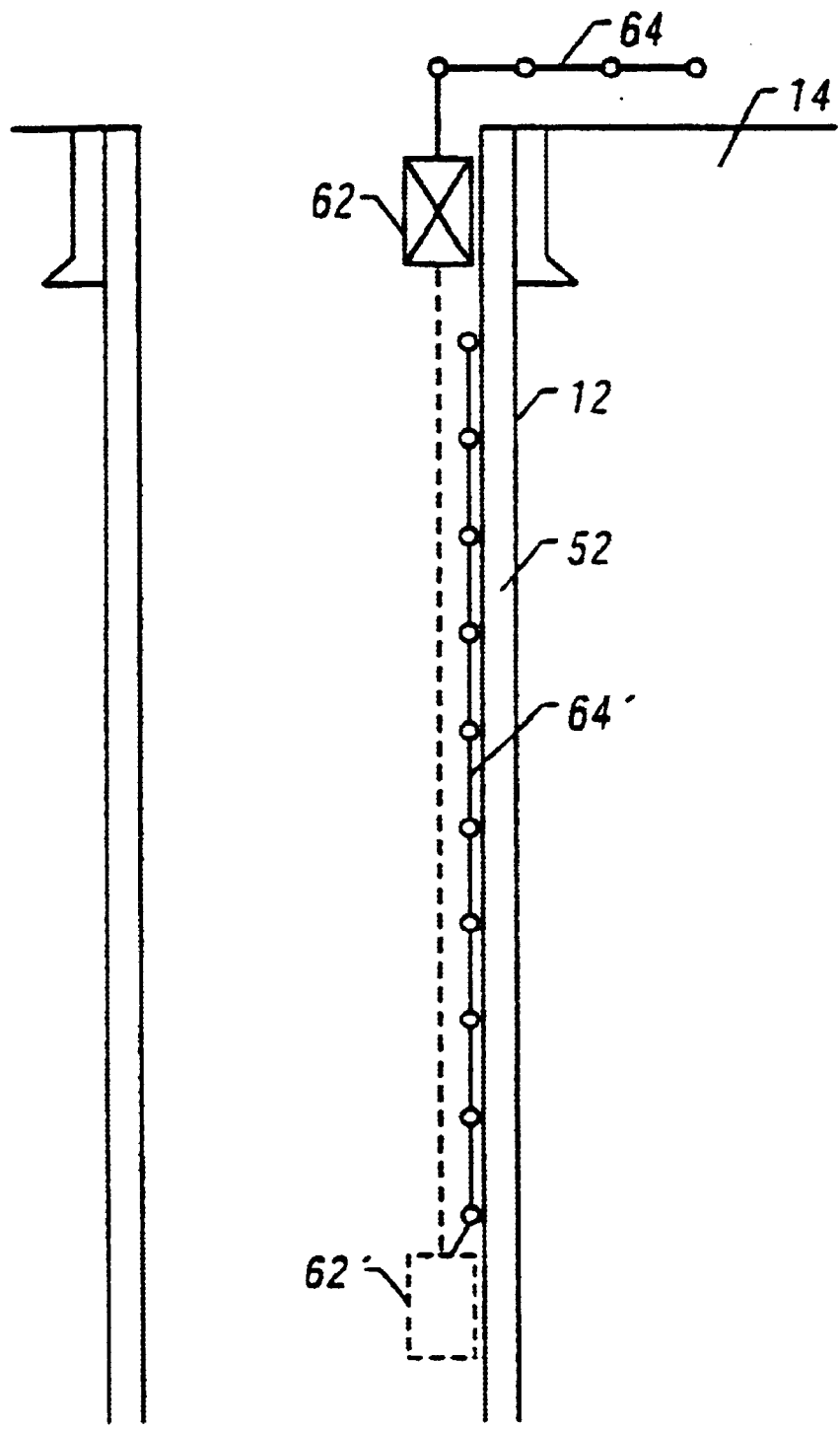
FIG. 1A shows the use of a robotic device for deployment of the fiber optic sensors.

The sensors 40 may be installed in the wellbores 12, 16 and 18 before or after installing casings in the wellbores, such as casings 52 shown installed in the wellbore 12. This may be accomplished by connecting the strings 41a and 41b along the inside castings 52. In such a method, the strings 41a and 41b are preferably connected end-to-end at the surface to ensure proper connections of the couplings 42. The fiber optic sensors 40 and/or strings 41a and 41b may be deployed or installed by conveying on coil tubing or pipes or other known methods. Alternatively, the fiber optic sensors may be conveyed and installed by robotics deices. This is illustrated in FIG. 1A where a robotic device 62 is shown with a string of sensors 64 attached to it. The robotic device proceeds down the wellbore 12 having a casing 52 therein to the position indicated by 62', deploying the string of sensors in the position indicated by 64'. In addition to installing sensors, the robotic device 64 may also perform other functions, such as monitoring the performance of the sensors, and communicating with other devices such as the DA, the LS/D and other downhole devices described below. The robotic devices may also be utilized to replace a sensor, conduct repairs and to retrieve the sensors or strings to the surface. Alternatively, the fiber optic sensors 40 may be placed in the casing 52 at the surface while individual casing sections (which are typically about forty feet long) are joined prior to conveying the casing sections into the borehole. Stabbing techniques for joining casing or tubing sections are known in the art and are preferred over rotational joints be stabbing generally provides better alignment of the end couplings 42 and also because it allows operators to test and inspect optical connections between segments for proper two-way transmission of light energy through the entire string 41.

In the system shown in FIG. 1, a plurality of fiber optic sensors 40 are installed spaced apart in one or more wellbores, such as wellbores 12, 16 and 18. If desired, each fiber optic sensor can operate in more than one mode to provide a number of different measurements. The light source 46a, and data detection and acquisition system 48a are preferably placed downhole. Although each fiber optic sensor 40 provides measurements for multiple parameters, it is relatively small compared to individual commonly used single measurement sensors, such as pressure sensors, strain gauges, temperature sensors, flow measurement devices and acoustic sensors. This makes it possible to make a large number of different types of measurements utilizing relatively little space downhole. Installing data acquisition and processing devices or units 48a downhole allows making a large number of data computations and processing downhole, avoiding the need for transmitting large amounts of data to the surface. Installing the light source 46a downhole allows locating the source 46a close to the sensors 40, which avoids transmission of light over great distances from the surface. The data from the downhole acquisition system 48a may be transmitted to the surface by any suitable method including wireline connectors, electromagnetic telemetry, and acoustic methods. Still, in some applications, it may be desirable to locate the light source 46b and/or the data acquisition and processing system 46b at the surface. Also, in some cases, it may be more advantageous to partially process the data downhole and partially at the surface.

Still referring o FIG. 1, any number of other sensors, generally denoted herein by numeral 60 may be disposed in any of the wellbores 12, 16 and 18. Such sensors may include sensors for determining the resistivity of fluids and formations, gamma ray sensors and hydrophones. The measurements from the fiber optic sensors 40 and sensors 60 are combined to determine the various conditions downhole. For example, flow measurements from production zones and the resistivity measurements may be combined to determine water saturation or to determine oil, gas and water content.

In one mode, the fiber optic sensors are permanently installed in the wellbores at selected locations. In a producing wellbore, the sensors 40 continuously or periodically (as programed) provide the pressure and/or temperature and/or fluid flow measurements. Such measurements are preferably made for each producing zone in each of the wellbores. To perform certain types of reservoir analysis, it is required to know the temperature and pressure build rates in the wellbores. This requires measuring temperature and pressure at selected locations downhole over extended time periods after shutting down the well at the surface. In prior art methods, the well is shut down, a wireline tool is conveyed into the wellbore and positioned at one location in the wellbore. The tool continuously measures temperature and pressure and may provide other measurements, such as flow rates. These measurements are then utilized to perform reservoir analysis, which may included determining the extent of the hydrocarbon reserves remaining in a field, flow characteristics of the fluid from the producing formation, water it etc. The above described prior art methods do not provide continuous measurements while the well is producing and require special wireline tools to be conveyed into the borehole The present invention, on the other hand provides, in-situ measurements while the well is producing. The fluid flow information from each zone is used to determine the effectiveness of each producing zone. Decreasing flow rates over time indicate problems with the flow control devices, such as screens and sliding sleeves, or clogging of the perforations and rock matrix near the wellbore. This information is used to determine the course of action, which may include further opening or closing sliding sleeves to increase or decrease production rates, remedial work, such as cleaning or reaming operations, shutting down a particular zone, etc. This is discussed below in reference to FIGS. 2–13. The temperature and pressure measurements are used to continually monitor each production zone and to update reservoir models. To make measurements determining the temperature and build-up rates, the wellbores are shut down and the process of making measurements continues. This does not require transporting wherein tools to the location, something that can be very expensive at offshore locations and wellbores drilled in remote locations Furthermore, in-situ measurements and computed data can be communicated to a central office or the offices of the logging and reservoir engineers via satellite. This continuous monitoring of wellbores allows taking relatively quick action, which can significantly improve the hydrocarbon production and the life of the wellbore. The above described methods may also be taken for non-producing zones, such as zone II, to aid in reservoir modeling, to determine the effect of production from various wellbores on the field in which the wellbores are being drilled.

Figure 2:
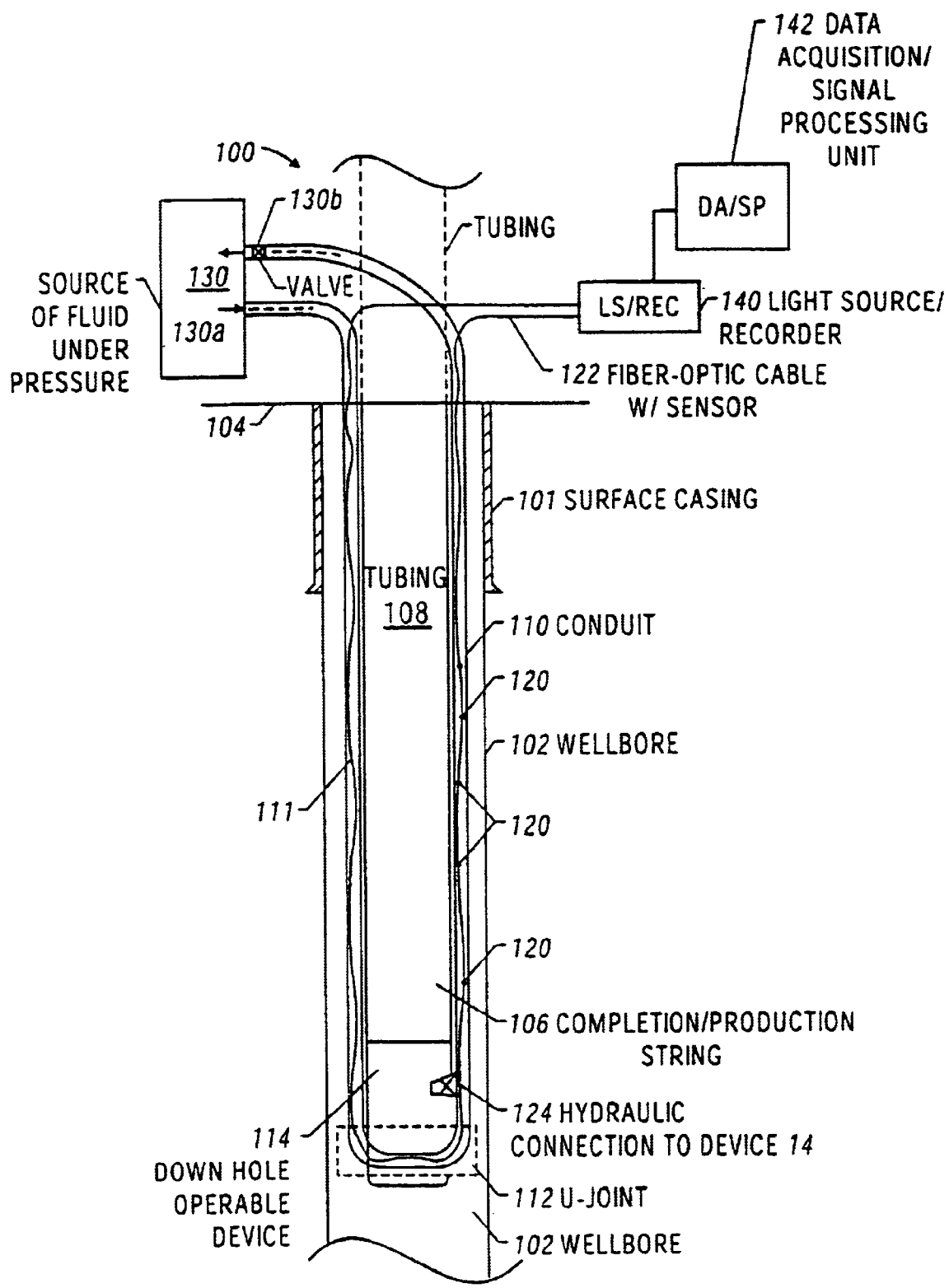
FIG. 2 is a schematic illustration of a wellbore system wherein a fluid conduit along a string placed in the wellbore is utilized for activating a hydraulically-operated device and for deploying a fiber optic cable having a number of sensors along its length according to one preferred embodiment of the present invention.

FIG. 2 is a schematic diagram of a wellbore system 100 according to one embodiment of the present invention. System 100 includes a wellbore 102 having a surface casing 101 installed a short distance from the surface 104. After the wellbore 102 has been drilled to a desired depth, a completion or production string 106 is conveyed into the wellbore 102. The string 106 includes at least one downhole hydraulically operable device 114 carried by a tubing 108 which tubing may be a drill pipe, coiled tubing or production tubing. A fluid conduit 110 having a desired inner diameter 111 is placed or attached either on the outside of the string 106 (as shown in FIG. 2) or in the inside of the string (not shown). The conduit 110 is routed at a desired location on the string 106 via a u-joint 112 so as to provide a smooth transition for returning the conduit 110 to the surface 104. A hydraulic connection 124 is provided from the conduit 110 to the device 114 so that a fluid under pressure can pass from the conduit 110 to the device 114.

After the string 106 has been placed or installed at a desired depth in the wellbore 102, an optical fiber 112 is pumped inlet 130a under pressure by a source of fluid 130.

The optical fiber 122 passes through the entire length of the conduit 110 and returns to the surface 104 via outlet 130b. The fiber 122 is then optically coupled to a light source and recorder (or detector) (LS/REC) 140. A data acquisition/signal processor (DA/SP) 142 processes data/ received via the optical fiber 122 and also controls the operation of the light source and recorded 140.

The optical fiber 122 includes a plurality of sensors 120 distributed along its length. Sensors 120 may include temperature sensors, pressure sensors, vibration sensors or any other fiber optic sensor that can be placed on the fiber optic cable 122. Sensors 120 are formed into the cable during the manufacturing of the cable 122. The downhole device 114 may be any downhole fluid-activated device and may be a valve, a sliding sleeve, a perforating device, a packer or any other hydraulically-activated device. The downhill device is activated by supplying fluid under pressure through the conduit 110. Details of the sensor arrangement were described above with reference to FIGS. 1–1A.

Thus, the system 100 includes a hydraulic-control line in conduit 110 carried on a string 106. The control line 110 receives fiber optic cable 122 throughout its length and is connected to surface instrumentation 140 and 142 for distributed measurements of downhole parameters along its length, such as temperature, pressure, etc. The conduit 106 also carries fluid under pressure from a source of fluid under pressure 130 for operating a fluid-actuated device 114 such as a sliding sleeve, connected to the line 110. The line 110 may be arranged downhole along the string 106 in a V or other convenient shape. The fluid-actuated device 114 may also be a choke, fluid flow regulation device, packer, perforating gun or other completion and or production device.

During the completion of the wellbore 102, the sensors 120 provide useful measurements relating to their associated downhole parameters and the line 106 is used to actuate a downhole device. The sensors 120 continue to provide information schematic illustration on about the downhole parameters over time, as discussed above with reference to FIGS. 1–1A.

Figure 3:
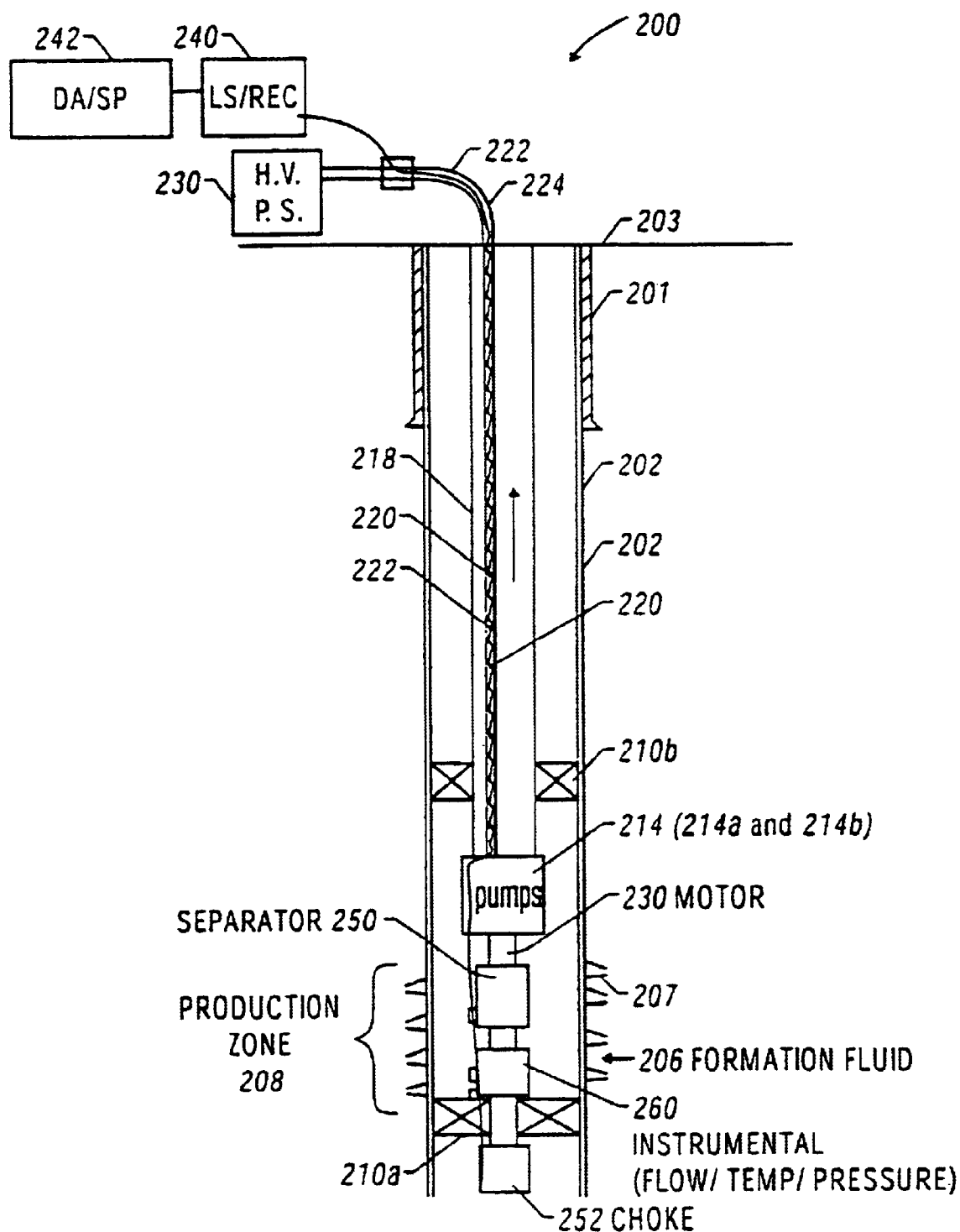
FIG. 3 shows a schematic of a producing well wherein a fiber optic cable with sensors is utilized to determine the health of downhole devices and to make measurements downhole relating to such devices and other downhole parameters.

Another part of the invention is related to the control of downhole devices using optical fibers. FIG. 3 shows a schematic diagram of a producing well 202 that preferably has two electric submersible pumps ("ESP") 214, one for pumping the oil/gas 206 the surface 203 and the other to pump any separated water back into a formation. The formation fluid 206 flows from a producing zone 208 into the wellbore 202 via perforations 207. Packers 210a and 210b installed below and above the ESP 214 force the fluid 206 to flow to the surface 203 via pumps ESP 214. An oil water separator 250 separates the oil and water and provide them to their respective pumps 214a–214b. A choke 252 provides desired back pressure. An instrument package 260 and pressure sensor is installed in the pump string 218 to measure related parameters during production. The present invention utilizes optical fiber with embedded sensors to provide measurements of selected parameters, such as temperature, pressure, vibration, flow rate as described below. ESPs 214 run at very high voltage which is supplied from a high voltage source 230 at the surface via a high voltage cable 224. Due to the high power carried by the cable 224, electrical sensors are generally not placed on or along side the cable 224.

In one embodiment of the present invention as shown in FIG. 3, a fiber optic cable 222 carrying sensors 220 is placed along the power cable 224. The fiber optic cable 222 is extended to below the ESPs 214 to the sensors in the instrumentation package 260 and to provide control to the devices, if desired. In one application, the sensors 220 measure vibration and temperature of the ESP 214. It is desirable to operate the ESP at a low temperature and without excessive vibration. The ESP 214 speed is adjusted so as to maintain one or both such parameters below their predetermined maximum value or within their respective predetermined ranges. The fiber optic sensors are used in this application to continuously or periodically determine the physical condition (health) of the ESP. The fiber optic cable 222 may be extended or deployed below the ESP at the time of installing the production string 218 in the manner described with respect to FIG. 2. Such a configuration may be utilized to continuously measure downhole parameters, monitor the health of downhole devices and control downhole devices.

Figure 4:
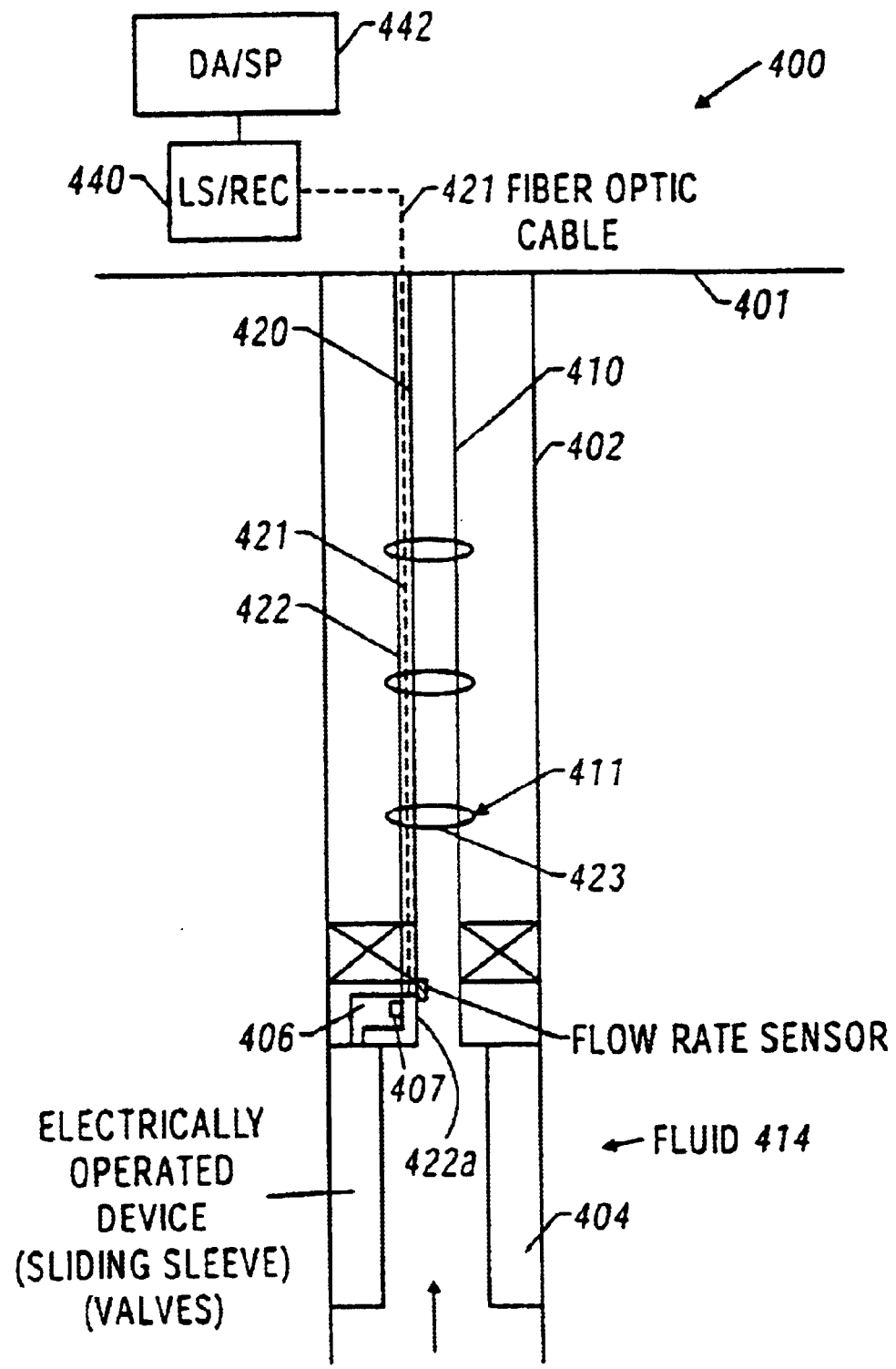
FIG. 4 is a schematic illustration of a wellbore system wherein a permanently installed electrically-operated device is operated by a fiber optic based system.

FIG. 4 shows a schematic of a wellbore system 400 wherein a permanently installed electrically-operated device is operated by a fiber optic based system. The system 400 includes a wellbore 402 and an electrically-operated device 404 installed at a desired depth, which may be a sliding sleeve, a choke, a fluid flow control device etc. An electric control unit 406 controls the operation of the device 404. A production tubing 410 installed above the device 404 allows formation fluid to flow to the surface 401. During the manufacture of the string 411 that includes the device 404 and the tubing 410, a conduit 422 is clamped along the length of the tubing 410 with clamps 423. An optical coupler 407 is provided at the electrical control unit 406 which can mate with a coupler fed through the conduit 422.

Either prior to or after placing the string 410 in the wellbore 402, a fiber optic cable 421 is deployed in the conduit 422 so that a coupler 422a at the cable 421 end would couple with the coupler 407 of the control unit 406. A light source 440 provides the light energy to the fiber 422. A plurality of sensors 420 may be deployed along the fiber 422 as described before. A sensor preferably provided on the fiber 422 determines the flow rate of formation fluid 414 flowing through the device 404. Command signals are sent by DA/SP 442 to activate the device 404 via the fiber 422. These signals are detected by the control unit 406, which in turn operate the device 404. This, in the configuration of FIG. 4, fiber optics is used to provide two way communication between downhole devices and sensors and a surface unit and to operate downhole devices.

Figure 5:
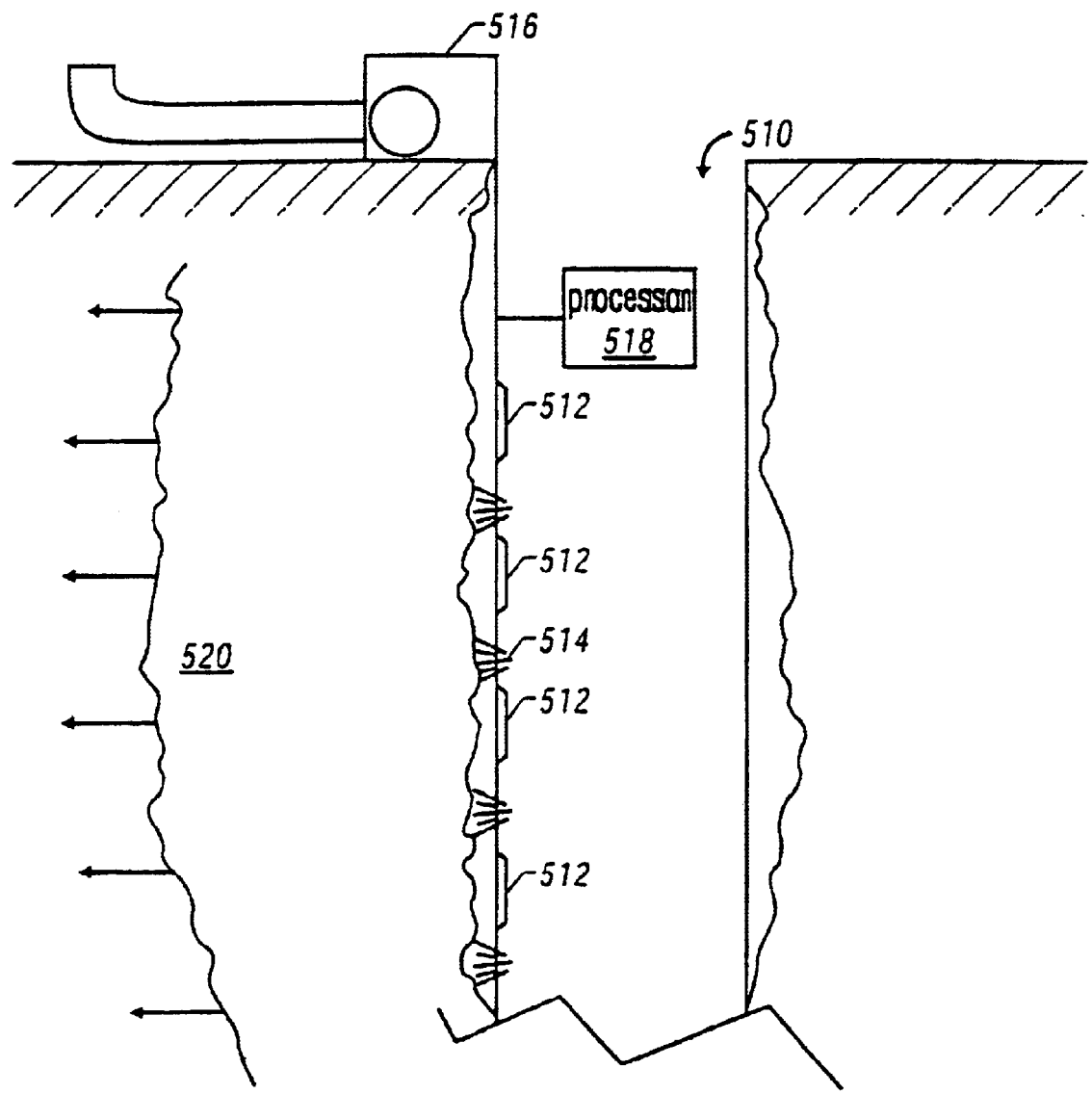
FIG. 5 is a schematic representation of an injection well illustrating a plurality of sensors mounted therein.

A particular application of the invention is in the control of downhole devices in secondary recovery options. Referring to FIG. 5, one of ordinary skill in the art will appreciate a schematic representation of an injection well 510. Also recognizable will be the representation of a flood front 520 which emanates from the injection well and is intended to progress toward a production well. This is also well represented in FIG. 6 of the present application. In the present invention at least one and, preferably, a plurality of sensors 512 are located permanently installed in the injection well and which are connected via the electrical wire cabling or fiber optic cabling to a processor which may either be a downhole processor or a surface processor. The system provides immediate real time information regarding the condition of the fluid front having been injected into the formation by the injection well. By carefully monitoring parameters such as conductivity, fluid density, pressure at the injection ports 514 or at the pump 516 (which while represented at the surface can be positioned downhole as well), acoustics and fluorescence for biological activity, one can ascertain significant information about the progress of the flood front such as whether the front has hit a barrier or whether the font may have "fingered" resulting in a likely premature breakthrough. This information is extremely valuable to the operator in order to allow remedial measures to prevent occurrences that would be detrimental to the efficiency of the flooding option. Remedial actions include the opening or closing of chokes or other valves in increments or completely in order to slow down particular areas of injection or increase the speed of particular areas of injection in order to provide the most uniform flood front based upon the sensed parameters. These remedial measures can be take either by personnel at the surface directing such activity or automatically upon command by the surface control/processor on downhole processing unit 518. The sensors contemplated herein may be in the injection well or in both the injection well and the production well. They are employed in several different methods to obtain information such as that indicated above.

Control is further heightened in an embodiment by providing a link between downhole sensors in the production well to the downhole sensors in the injection well as well as a connection to the flow control tools in both well. By providing the operable connections to all of these parts of the system the well can actually run itself and provide the most efficient oil recovery based upon the creation and maintenance of a uniform flood front. It will be understandable at this point to one of ordinary skill in the art that the flood front can be regulated from both sides of FIG. 2 i.e., the injection well and the production well by opening production well valves in areas where the flood front is lagging while closing valves in areas where the flood front is advancing.

Complementary to this, the fluid injection valves e.g., sliding or rotating sleeves, etc. would be choked or closed where the flood front is advancing quickly and opened more where the flood front is advancing slowly. This seemingly complex set of circumstances is easily controlled by the system of the invention and rapidly remedies any abnormalities in the intended flood profile. Sweep efficiency of the steam or other fluid front is greatly enhanced by the system of the invention. All of the sensors contemplated in the production well and the injection well are, preferably, permanently installed downhole sensors which are connected to processors and/to one another by electrical cabling or fiber optic cabling.

Figure 7:
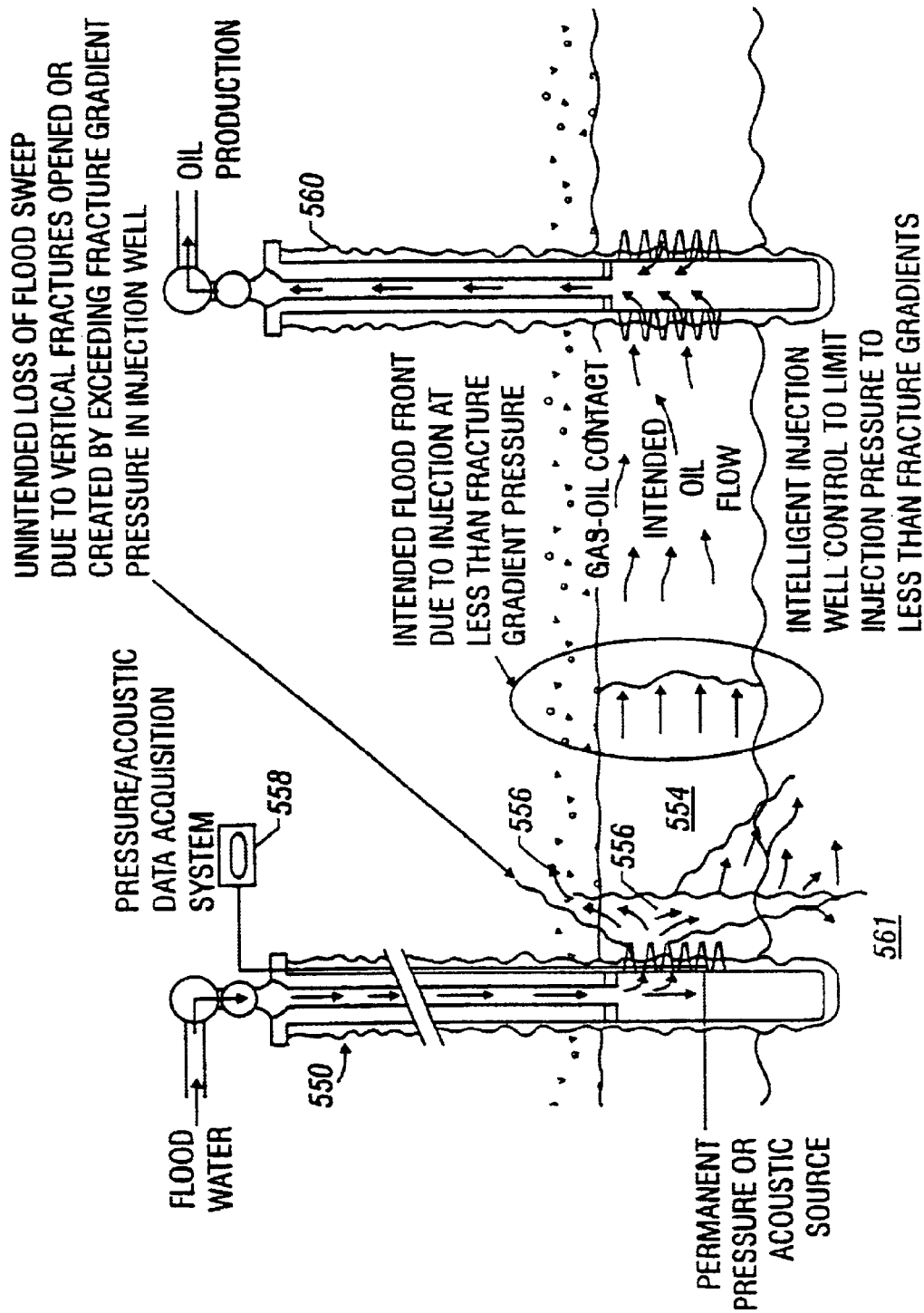
FIG. 7 is a schematic representation similar to FIG. 6 but illustrating fluid loss through unintended fracturing.

In another embodiment of the invention, illustrated schematically in FIG. 7, downhole sensors measure strain induced in the formation by the injected fluid. Strain is an important parameter for avoiding exceeding the formation parting pressure or fracture pressure of the formation with the injected fluid. By avoid the opening of or widening of natural pre-existing fractures large unswept areas of the reservoir can be avoided. The reason this on is information is important regulation of pressure of the fluid to avoid such activity is that when pressure open fractures or new are created there is a path of much less or resistance for the fluid to run through. Thus as stated earlier, since the injection fluid will follow the path of least it would generally run in the fractures and around areas of the reservoir that need to be swept. Clearly this substantially reduces its efficiency. The situation is generally referred to in the art as an "artificially high permeability channel." Another detriment to such a condition is the uncontrolled loss of injected fluids. This is clearly a loss of oil due to the reduced efficiency of the sweep and additionally may function as an economic drain due to the loss of expensive fluids.

FIG. 7 schematically illustrates the embodiment and the condition set forth above by illustrating an injection well 550 and a production well 560. Fluid 552 is illustrated escaping via the unintended fracture from the formation 554 into the overlying gas cap level 556 and the underlying water table 561 and it is evident to one of ordinary skill in the art that the fluid is being lost in this location. The condition is avoided by the invention by using pressure sensors to limit the injection fluid pressure as described above. The rest of the fluid 552 is progressing as it is intended to through the formation 554. In order to easily and reliably determine what the stress is in the formation 554, acoustic sensors 556 are located in the injection well 550 at various points therein. Acoustic sensors which are well suited to the task to which they will be put in the present invention are commercially available from System Innovations, Inc., Spectris Corporation and Falmouth Scientific, Inc. The acoustic sensors pick up sounds generated by stress in the formation which propagate through the reservoir fluids or reservoir matrix to the injection well. In general, higher sound levels would indicate severe stress in the formation and should generate a reduction in pressure of the injected fluid whether by automatic control or by technician control. A data acquisition system 558 is preferable to render the system extremely reliable and system 558 may be at the surface where it is illustrated in the schematic drawing or may be downhole. Based upon acoustic signals received the system of the invention, preferably automatically, although manually is workable, reduces pressure of the injected fluid by ring pump pressure. Maximum sweep efficiency is thus obtained.

Figure 8:
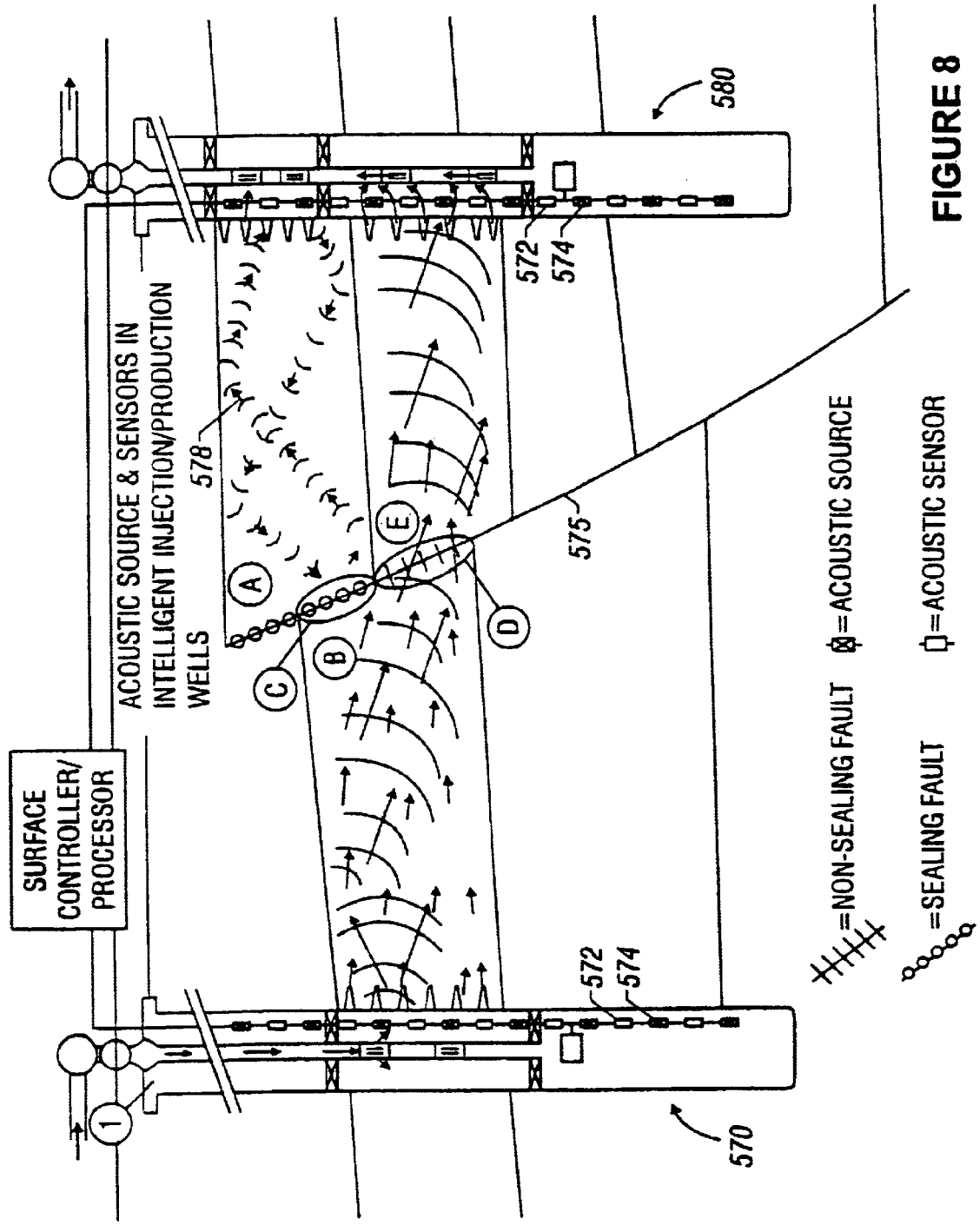
FIG. 8 is a schematic representation of an injection production well system where the wells are located on either side of a fault.

In yet another embodiment of the invention, as schematically illustrated in FIG. 8, acoustic generators and receivers are employed to determine whether a formation which is bifurcated buy a fault is sealed along the fault or is permeable along the fault. It is known by one of ordinary skill in the art that different strata within a formation bifurcated by a fault may have some zones that flow and some zones that are sealed; this is the illustration of FIG. 8. Referring directly to FIG. 8, injection well 570 employs a plurality of sensors 72 and acoustic generators 574 which, most preferably, alternate with increasing depth in the wellbore. In production well 580, a similar arrangement of sensor 572 and acoustic generators 574 are positioned. The sensors and generators are preferably connected to processors which are either downhole or on the surface and preferably also connect to the associated production or injection well. The sensors 572 can receive acoustic signals that are naturally generated in the formation, generated by virtue of the fluid flowing through the formation from the injection well and to the production well and also can receive signals which are generated by signal generators 574. Where signal generators 574 generate signals, the reflected signals that are received by sensors 572 over a period of time can indicate the distance and acoustic volume through which the acoustic signals have traveled. This is illustrated in area A of FIG. 8 in that the fault line 575 is sealed between area A and area B on the figure. This is illustrated for purposes of clarity only by providing circles 576 along fault line 575. Incidentally, the areas of fault line 575 which are permeable are indicated by hash marks 577 through fault line 575. Since the acoustic signal represented by arrows and semi-curves and indicated by numeral 578 cannot propagate through the area C of the drawing which bifurcates area A from area B on the left side of the drawing, that signal will bounce and it the can be picked up by sensor 572. The time delay, number and intensity of reflections and mathematical interpretation which is common in the art provides an indication of the lack of pressure transmissibility between those two zones. Additionally this pressure transmissibility can be confirmed by the detection by said acoustic signals by sensors 572 in the production well 580. In the drawing the area directly beneath area A is indicated as area E is permeable to area B through fault 575 because the region D in that area is permeable and will allow flow of the flood front from the injection well 570 through fault line 575 to the production well 580. Acoustic sensors and generators can be employed her as well since the acoustic signal will travel through the area D and, therefore, reflection intensity to the receivers 572 will decrease. Time delay will increase. Since the sensors and generators are connected to a central processing unit and to one another it is a simple operation to determine that the signal, in fact, traveled from one well to the other and indicates permeability throughout a particular zone. By processing the information that the acoustic generators and sensors can provide the injection and production wells can run autonomically by determining where fluids can flow and thus opening and closing valves at relevant locations on the injection well and production well in order to flush production fluid in a direction advantageous to run through a zone of permeability along the fault.

Other information can also be generated by this alternate system of the invention since the sensors 572 are clearly capable of receiving not only the generated acoustic signal but naturally occurring acoustic waveforms arising from both the flow of the injected fluids as the injection well and from those arising within the reservoirs in result of both fluid injection operations and simultaneous drainage of the reservoir in resulting production operations. The preferred permanent deployment status of the sensors and generators of the invention permit and see to the measurements simultaneously with ongoing injection flooding and production operations. Advancements in both acoustic measurement capabilities and signal processing while operating the flooding of the reservoir represents a significant, technological advance in that the prior art requires cessation of the injection/production operations in order to monitor acoustic parameters downhole. As one of ordinary skill in the art will recognize the cessation of injection results in natural redistribution of the active flood profile due primarily to gravity segregation of fluids and entropic phenomena that are not present during active flooding operations. This clearly also the possibility of premature breakthrough, as oil migrates to the relative top of the formation and the injected fluid, usually water, migrates to the relative bottom of the formation, there is a significant possibility that the water will actually reach the production well and thus further pumping of steam or water will merely run underneath the layer of oil at the top of the formation and the sweep of that region would be extremely difficult thereafter.

In yet another embodiment of the invention fiber optics are employed (similar to those disclosed in the U.S. application Ser. No. 60/048,989 filed on Jun. 9, 1997 (which is fully incorporated by reference) to determine the amount of and/or presence of befouling within the reservoir by providing a culture chamber within the injection or production well, wherein light of a predetermined wavelength may be injected by a fiber optical cable, irradiating a sample determining the degree to which biofouling may have occurred. As one of ordinary skill in the art will recognize, various biofouling organisms will have the ability to fluoresce at a given wavelength, that wavelength once determined, is useful for the purpose above stated.

Figure 6:
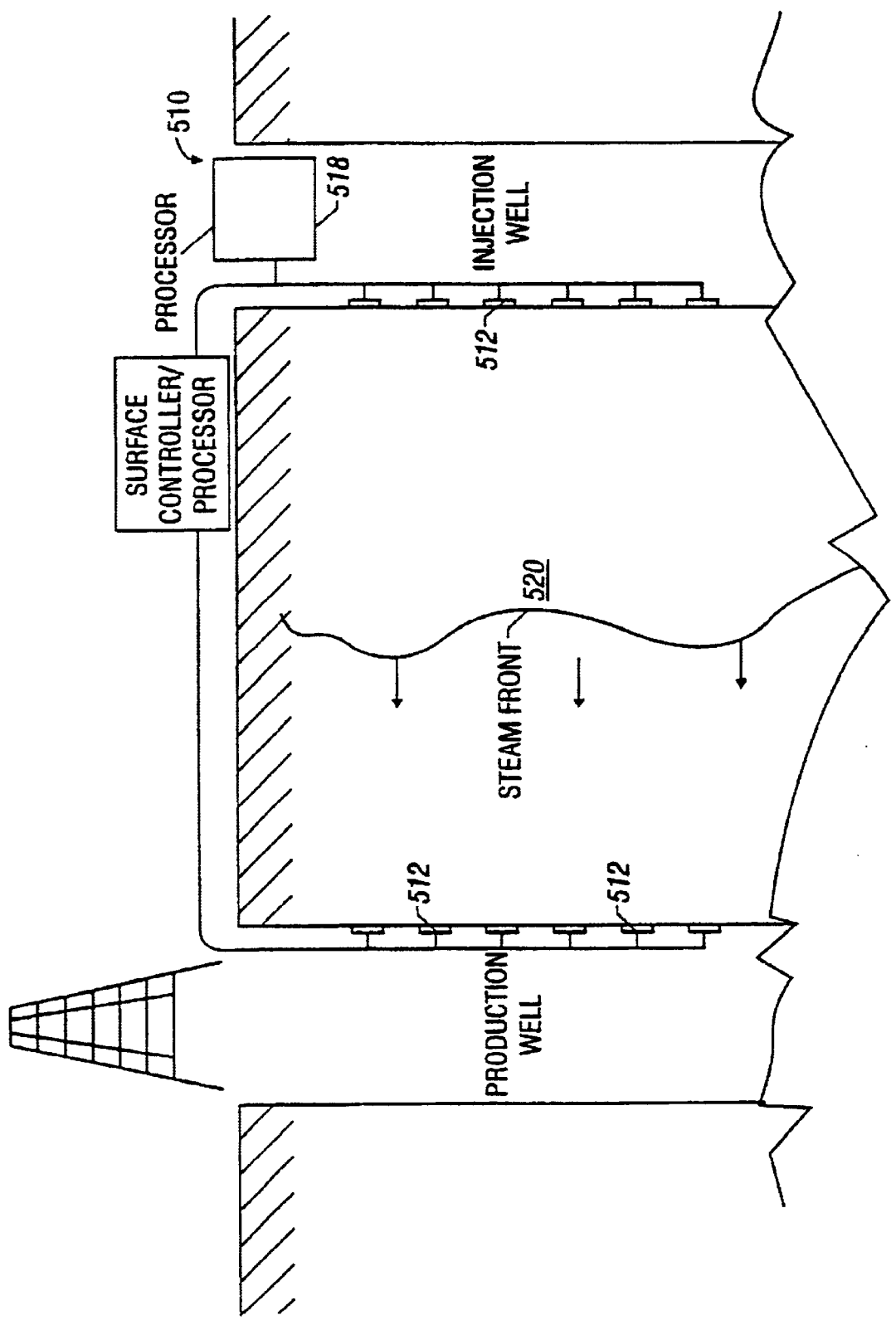
FIG. 6 is a schematic representation illustration both an injection well and a production well having sensors and a flood front running between the wells.

In another embodiment of the invention, the flood front is monitored from the "back" employing sensors installed in the injection well. The sensors which are adequately illustrated in FIGS. 5 and 6 provide acoustic signals which reflect from the water/oil interface thus providing an picture in a moment in time of the three-dimensional flood front. Taking pictures in 4-D i.e., three dimensions over real time provides an accurate format of the density profile of the formation due to the advancing flood front. Thus, a particular profile and the relative advancement of the front can be accurately determined by the density profile changes. It is certainly possible to limit the sensors and acoustic generators to the injection well for such a system, however it is even more preferable to also introduce sensors and acoustic generators in the production well toward which the front is moving thus allowing an immediate double check of the fluid front profile. That is, acoustic generators on the production well will reflect a signal off the oil/water interface and will provide an equally accurate three-dimensional fluid front indicator. The indicators from both sides of the front should agree and thus provides an extremely reliable indication of location and profile.

Figure 9:
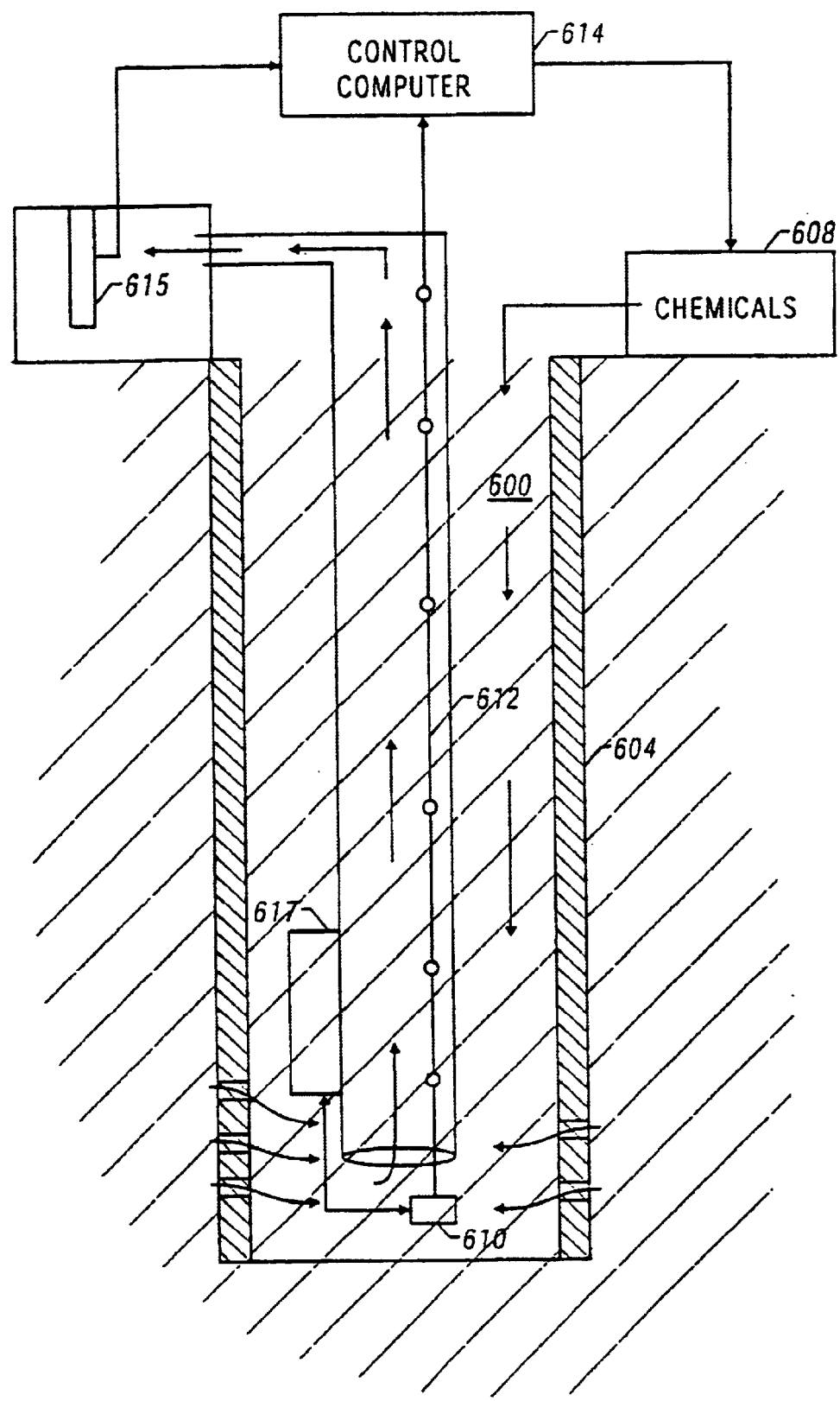
FIG. 9 is a schematic illustration of a chemical injection monitoring and control system utilizing a distributed sensor arrangement and downhole chemical monitoring sensor system in accordance with the present invention.

Referring now to FIG. 9, the distributed fiber optic sensors of the type described above are also well suited for use in a production well where chemicals are being injected therein and there is a resultant need for the monitoring of such a chemical injection process so as to optimize the use and effect of the injected chemicals. Chemicals often need to be pumped down a production well for inhibiting scale, paraffins and the like as well as for other known processing applications and pretreatment of the fluids being produced. Often, as shown in FIG. 9, chemicals are introduced in an annulus 600 between the production tubing 602 and the casing 604 of a well 616. The chemical injection (shown schematically at 608) can be accomplished in a variety of known methods such as in connection with a submersible pump (as shown for example in U.S. Pat. No. 4,582,131, assigned to the assignee hereof and incorporated herein by reference) or through an auxiliary line with a cable used with an electrical submersible pump (such as shown for example in U.S. Pat. No. 5,528,824, assigned to the assignee hereof and incorporated herein by reference).

In accordance with an embodiment of the present invention, one or more bottomhole sensors 610 are located in the producing zone for sensing a variety of parameters associated with the producing fluid and/or interaction of the injected chemical and the producing fluid. Thus, the bottomhole sensors 610 will sense parameters relative to the chemical properties of the produced fluid such as the potential ionic content, the covalent content, pH level, oxygen levels, organic precipitates and like measurements. Sensors 610 can also measure physical properties associated with the producing fluid and/or the interaction of the injected chemicals and producing fluid such as the oil/water cut, viscosity and percent solids. Sensors 610 can also provide information related to paraffin and scale build-up, $H_2S$ content and the like.

Bottomhole sensors 610 preferably communicate with and/or are associated with a plurality of distributed sensors 612 which are positioned along at least a portion of the wellbore (e.g., preferably the interior of the production tubing) for measuring pressure, temperature and/or flow rate as discussed above in with FIG. 1. The present invention is also preferably associated with a surface control and monitoring system 614 and one or more known surface sensors 615 for sensing parameters related to the produced fluid; and more particularly for sensing and monitoring the effectiveness of treatment rendered by the injected chemicals. The sensors 615 associated with system 614 can sense parameters related to the content and amount of, for example, hydrogen sulfide, hydrates, paraffin, water, solids and gas.

Preferably, the production well disclosed in FIG. 9 has associated therewith a so-called "intelligent" downhole control and monitoring system which may include a downhole computerized controller 618 and/or the aforementioned surface control and monitoring system 614. This control and monitoring system is of the type disclosed in U.S. Pat. No. 5,597,042, which is assigned to the hereof and fully incorporated herein by reference. As disclosed in U.S. Pat. No. 5,597,042, the sensors in the "intelligent" production wells of this type are associated with downhole computer and/or surface controllers which receive information from the sensors and based on this information, initiate some type of control for enhancing or optimizing the efficiency of production of the well or in some other way effecting the production of fluids from the formation. In the present invention, the surface and/or downhole computers 614, 618 will monitor the effectiveness of the treatment of the injected chemicals and based on the sensed information, the control computer will initiate some change in the manner, amount or type of chemical being injected. In the system of the present invention, the sensors 610 and 612 may be connected remotely or in-situ.

In a preferred embodiment of the present invention, the bottomhole sensors comprise fiber optic chemical sensors. Such fiber optic chemical sensors preferably utilize fiber optic probes which are used as a sample interface to allow light from the fiber optic to interact with the liquid or gas stream and return to a spectrometer for measurement. The probes are typically composed of sol gel indicators. Sol gel indicators allow for on-line, real time measurement and control thought the use of indicator materials trapped in a porous, sol gel derived, glass matrix. Thin films of this material are coated onto optical components of various probe designs to create sensors for process and environmental measurements. These probes provide increased sensitivity to chemical species based upon characteristics of the specific indicator. For example, sol gel probes can measure with great accuracy the pH of a material and sol gel probes can also measure for specific chemical content. The sol gel matrix is porous, and the size of the pores is determined in by how the glass is prepared. The sol gel process can be controlled so as to create a sol gel indicator composite with pores small enough to trap an indicator in the matrix but large enough to allow ions of a particular chemical of interest to pass freely in and out and react with the indicator. An example of suitable sol gel indicator for use in the present invention is shown in FIGS. 10 and 11.

Figure 10:
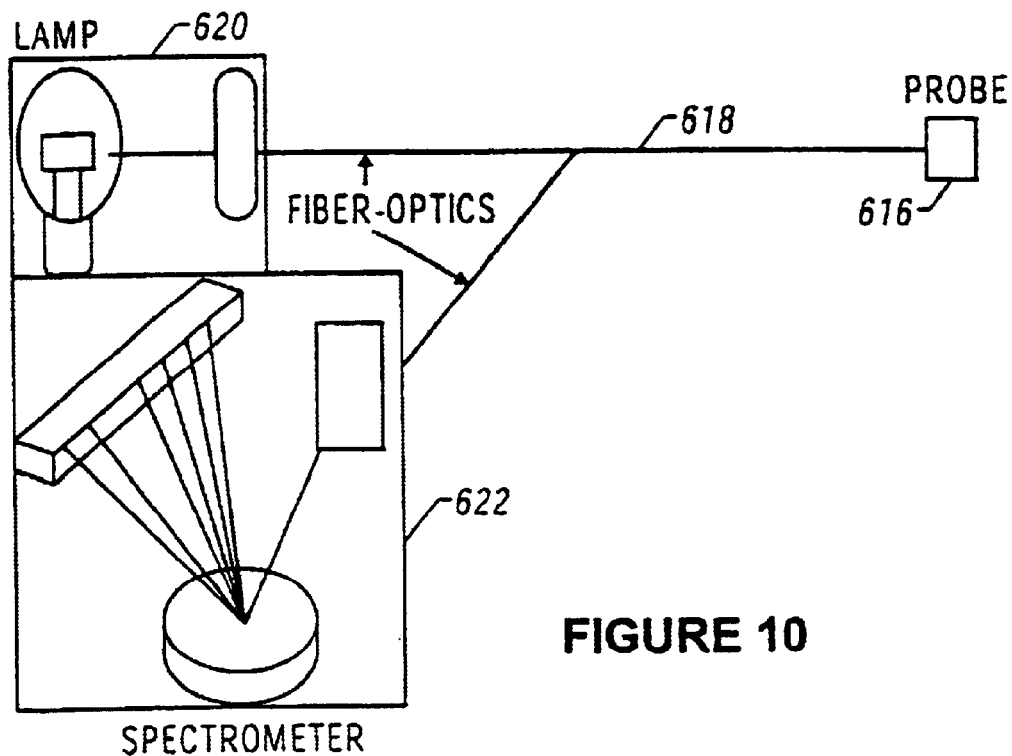
FIG. 10 is a schematic illustration of a fiber optic sensor system for monitoring chemical properties of produced fluids.
Figure 11:
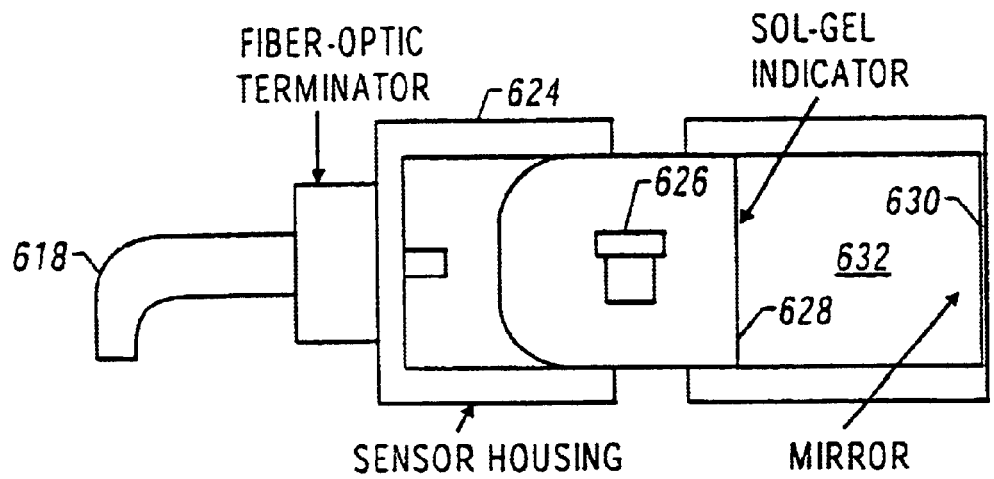
FIG. 11 is a schematic illustration of a fiber optic sol gel indicator probe for use with the sensor system of FIG. 10.

Referring to FIGS. 10 and 11, a probe is shown at 616 connected to a fiber optic cable 618 which is in turn connected both to a light source 620 and a spectrometer 622. As shown in FIG. 11, probe 616 includes a sensor housing 624 connected to a lens 626. Lens 626 has a sol gel coating 628 thereon which is tailored to measure a specific downhole parameter such as pH or is selected to detect the presence, absence or amount of a particular chemical such as oxygen, $H_2S$ or the like. Attached to and spaced from lens 626 is a mirror 630. During use, light from the fiber optic cable 618 is collimated by lens 626 whereupon the light passes through the sol gel coating 628 and sample space 632. The light is then reflected by mirror 630 and returned to the fiber optical cable. Light transmitted by the fiber optic cable is measured by the spectrometer 622. Spectrometer 622 (as well as light source 620) may be located either at the surface or at some location downhole. Based on the spectrometer measurements, a control computer 614, 616 will analyze the measurement and based on this analysis, the chemical injection apparatus 608 will change the amount (dosage and concentration), rate or type of chemical being injected downhole into the well. Information from the chemical injection apparatus to amount of chemical left storage, chemical quality level and the like will also be sent to the control computers. The control computer may also base its control decision on input received from surface sensor 615 relating to the effectiveness of the chemical treatment on the produced fluid, the presence and concentration of any impurities or undesired by-products and the like.

In addition to the bottomhole sensors 610 being comprise of the fiber optic sol gel type sensors, in addition, the distributed sensors 612 along production tubing 602 may also include the fiber optic chemical sensors (sol gel indicators) of the type discussed above. In this way, the chemical content of the production fluid may be monitored as it travels up the production tubing if that is desirable.

The permanent placement of the sensors 610, 612 and control system 617 downhole in the well leads to a significant advance in the field and allows for real time, remote control of chemical injections into a well without the need for wireline device or other well interventions.

Figure 12:
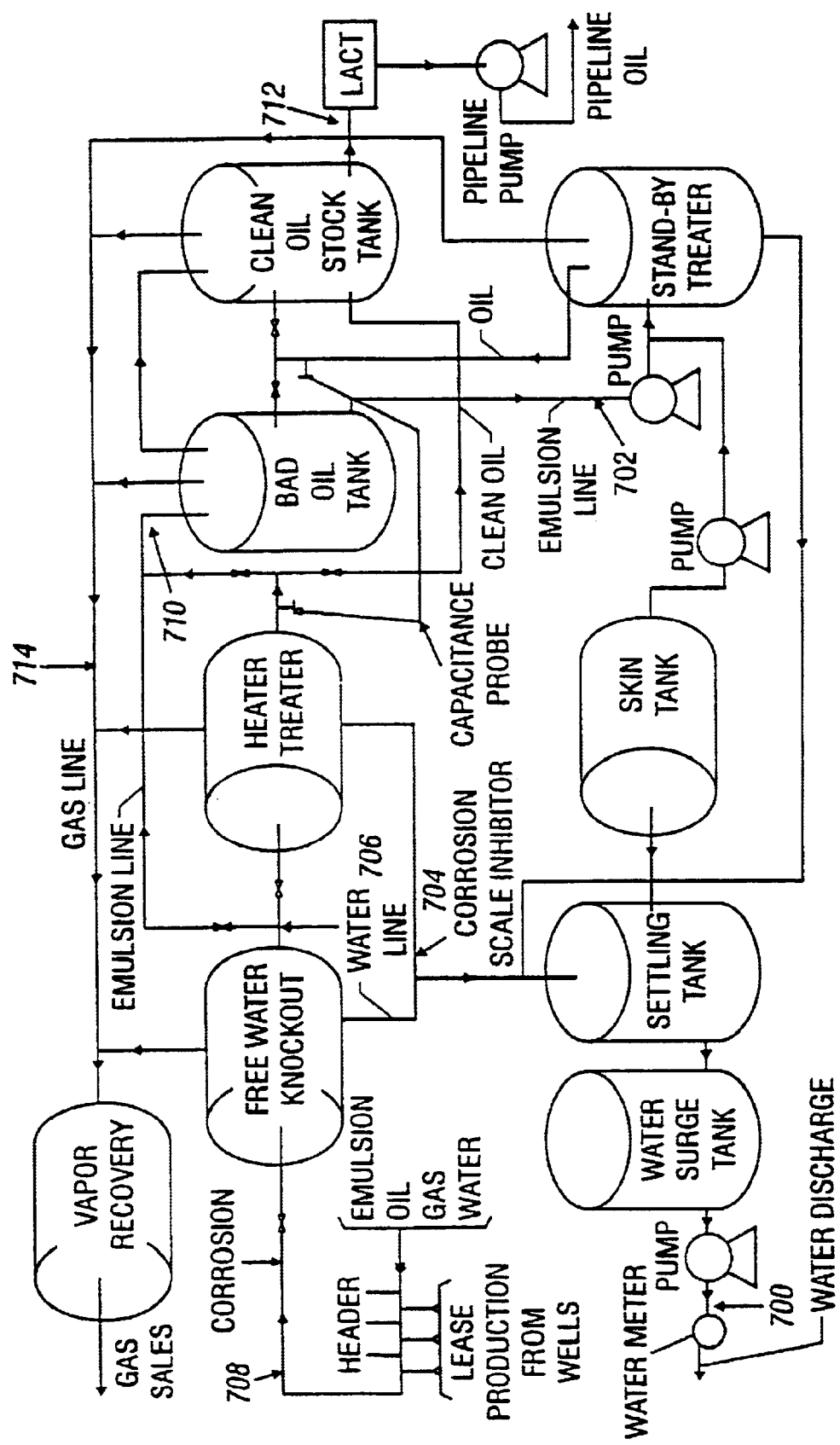
FIG. 12 is a schematic illustration of a system in accordance with the present invention.

In accordance with the present invention, a novel control and monitoring system is provided for use in connection with a treating system for handling produced hydrocarbons in an oilfield. Referring to FIG. 12, a typical surface treatment system used for treating produced fluid in oil fields is shown. As is well known, the fluid produced from the well includes a combination of emulsion, oil, gas and water. After these well fluids are produced to the surface, they are contained in a pipeline known as a "flow line". The flow line range in length from a few feet to several thousand feet. Typically, the flow line is connected directly into a series of tanks and treatment devices which are intended to provide separation of the water in emulsion from the oil and gas. In addition, it is intended that the oil and gas be separated for transport to the refinery.

The produced fluids flowing in the flow line and the various separation techniques which act on these produced fluids lead to serious corrosion problems. Presently, measurement of the rate of corrosion on the various metal components of the treatment systems such as the piping and tanks is accomplished by a number of sensor techniques including weight loss coupons, electrical resistance probes, electrochemical—linear polarization techniques, electrochemical noise techniques and AC impedance techniques. While these sensors are useful in measuring the corrosion rate of a metal vessel or pipework, these sensors do not provide any information relative to the chemicals themselves, that is the concentration, characterization or other parameters of chemicals introduced into the treatment system. These chemicals are introduced for a variety of reasons including corrosion inhibition and emulsion breakdown, as well as sale, wax, asphaltene, bacteria and hydrate control.

In accordance with an important feature of the present invention, sensors are used in chemical treatment systems of the type disclosed in FIG. 12 which monitors the chemicals themselves as opposed to the effects of the chemicals (for example, the rate of corrosion). Such sensors provide the operator of the treatment system with a real time understanding of the amount of chemical being introduced, the transport of that chemical throughout the system, the concentration of the chemical in the system and like parameters. Examples of suitable sensors which may be used to detect parameters relating to the chemicals traveling through the treatment system include the fiber optic sensor described above with to FIGS. 10 and 11 as well as other known sensors such as those sensors based on a variety of technologies including ultrasonic absorption and reflection, ad cavity spectroscopy (LIMS), X-ray fluorescence spectroscopy, neutron activation spectroscopy, pressure measurement, microwave or millimeter wave radar reflectance or absorption, and other optical and acoustic (i.e., ultrasonic or sonar) methods. A suitable microwave sensor for sensing moisture and other constituents in the solid and liquid phase influence and effluent streams is described in U.S. Pat. No. 5,455,516, all of the contents of which are incorporated herein by reference. An example of a suitable apparatus for sensing using LIBS is disclosed in U.S. Pat. No. 5,379,103 all of the contents of which are incorporated herein by reference. An example of a suitable apparatus for sensing using LIMS is the LASMA Laser Mass Analyzer available from Advanced Power Technologies, Inc. of Wash. D.C. An example of a suitable ultrasonic sensor is disclosed in U.S. Pat. No. 5,148,700 (all of the contents of which are incorporated herein by reference). A suitable commercially available acoustic sensor is sold by Entech Design, Inc., of Denton, Tex. under the trademark MAPS®. Preferably, the sensor is operated at a multiplicity of frequencies and signal strengths. Suitable millimeter wave radar techniques used in conjunction with the present invention are described in chapter 15 of Principles and Applications of Millimeter Wave Radar, edited by N. C. Currie and C. E. Brown, Artecn House, Norwood, Mass. 1987. The ultrasonic technology referenced above can be logically extended to millimeter wave devices.

While the sensors may be utilized in a system such as shown in FIG. 12 at a variety of locations, the arrows numbered 700, through 716 indica those positions where information relative to the chemical introduction would be especially useful.

Figure 13:
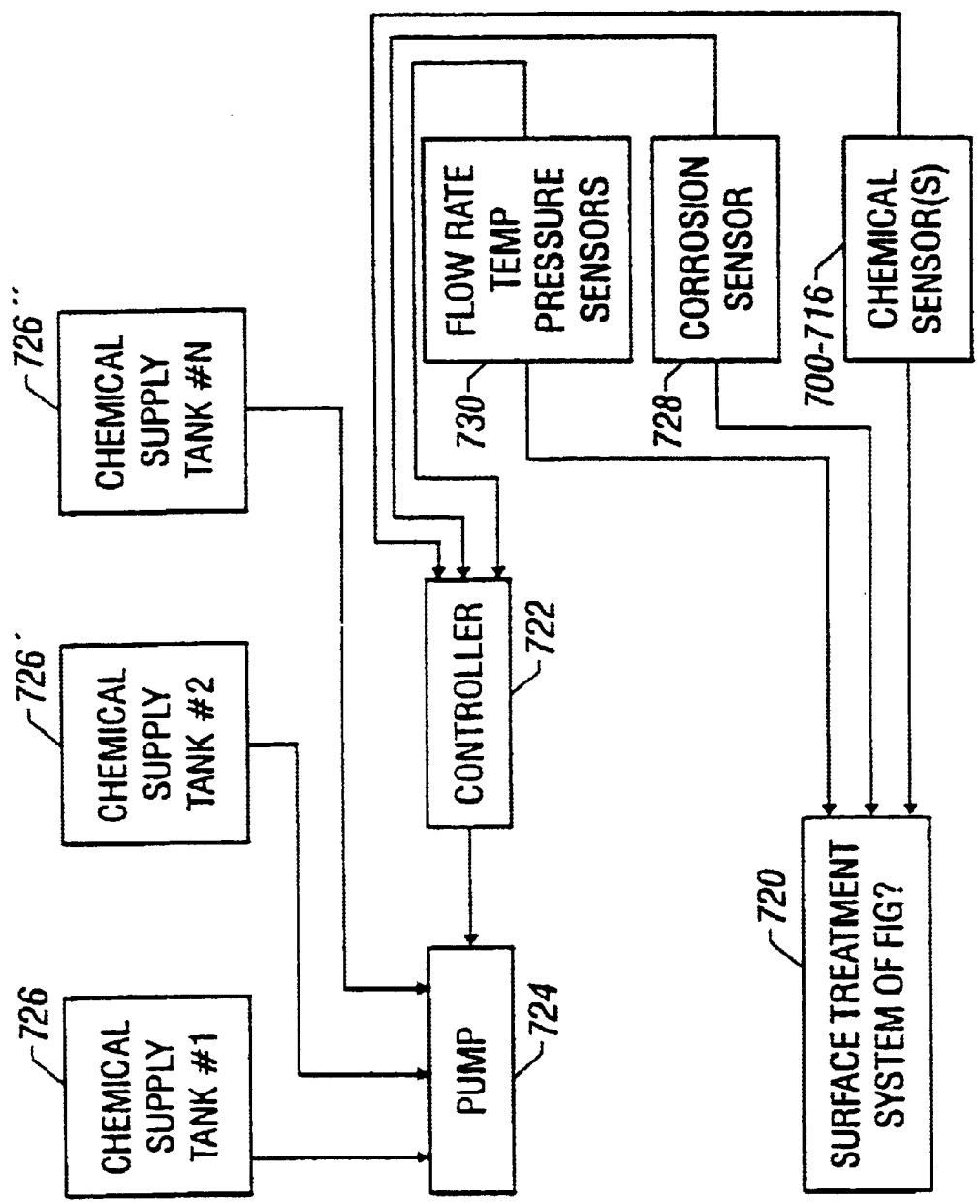
FIG. 13 is a schematic of a control and monitoring system for the surface treatment system of FIG. 12.

Referring now to FIG. 13, the surface treatment system of FIG. 12 is shown generally at 720. In accordance with the present invention, the chemical sensors (i.e. 700–716) will sense, in real, parameters (i.e., concentration and classification) related to the introduced chemicals and supply that sensed information to a controller 722 (preferably a computer or microprocessor based controller). Based on that sensed information monitored by controller 722, the controller will instruct pump or other metering device 724 to maintain, vary or otherwise alter the amount of chemical and/or type of chemical being added to the surface treatment system 720. The supplied chemical from tank 726, 726' and 726" can, of course, comprise any suitable treatment chemical such as those chemicals used to treat corrosion, break down emulsions, etc. Examples of suitable corrosion inhibitors include long chain aminos or aminidiazolines. Suitable commercially available chemicals include CronoxÔ which is a corrosion inhibitor sold by Baker Petrolite, a division of Baker-Hughes, Incorporated, of Houston, Tex.

Thus, in accordance with the control and monitoring system of FIG. 13, based on information provided by the chemical sensors 700–716, corrective measures can be taken for varying the injection of the chemical (corrosion inhibitor, emulsion breakers, etc.) into the system. The injection point of these chemical could be anywhere upstream of the location being sensed such as the location where the corrosion is being sensed. Of course, this injection point could include injections downhole. In the context of a corrosion inhibitor, the inhibitors work by forming a protective film on the metal and thereby prevent water and corrosive gases from corroding the metal surface. Other surface treatment chemicals include emulsion breaks which break the emulsion and facilitate water removal. In addition to removing a breaking emulsions, chemicals are also introduced break out and/or remove solids, wax, etc. Typically, chemicals are introduced so as to provide what is known as a base sediment and war (B. S. and W.) of less than 1%.

In addition to the parameters relating to the chemical introduction being sensed by chemical sensors 700–716, the monitoring and control system of the present invention can also utilize known corrosion measurement devices as well including flow rate, temperature and pressure sensors. These other sensors are schematically shown in FIG. 13 at 728 and 730. The present invention thus provides a means for measuring parameters related to the introduction of chemicals into the system in real time and on line. As mentioned, these parameters include chemical concentrations may also include such chemical properties as potential ionic content, the covalent content, pH level, oxygen levels, organic precipitates and like measurements. Similarly, oil/water cut viscosity and percent solids can be measured as will as paraffin and scale build-up, $H_2S$ content and the like.

Figure 14:
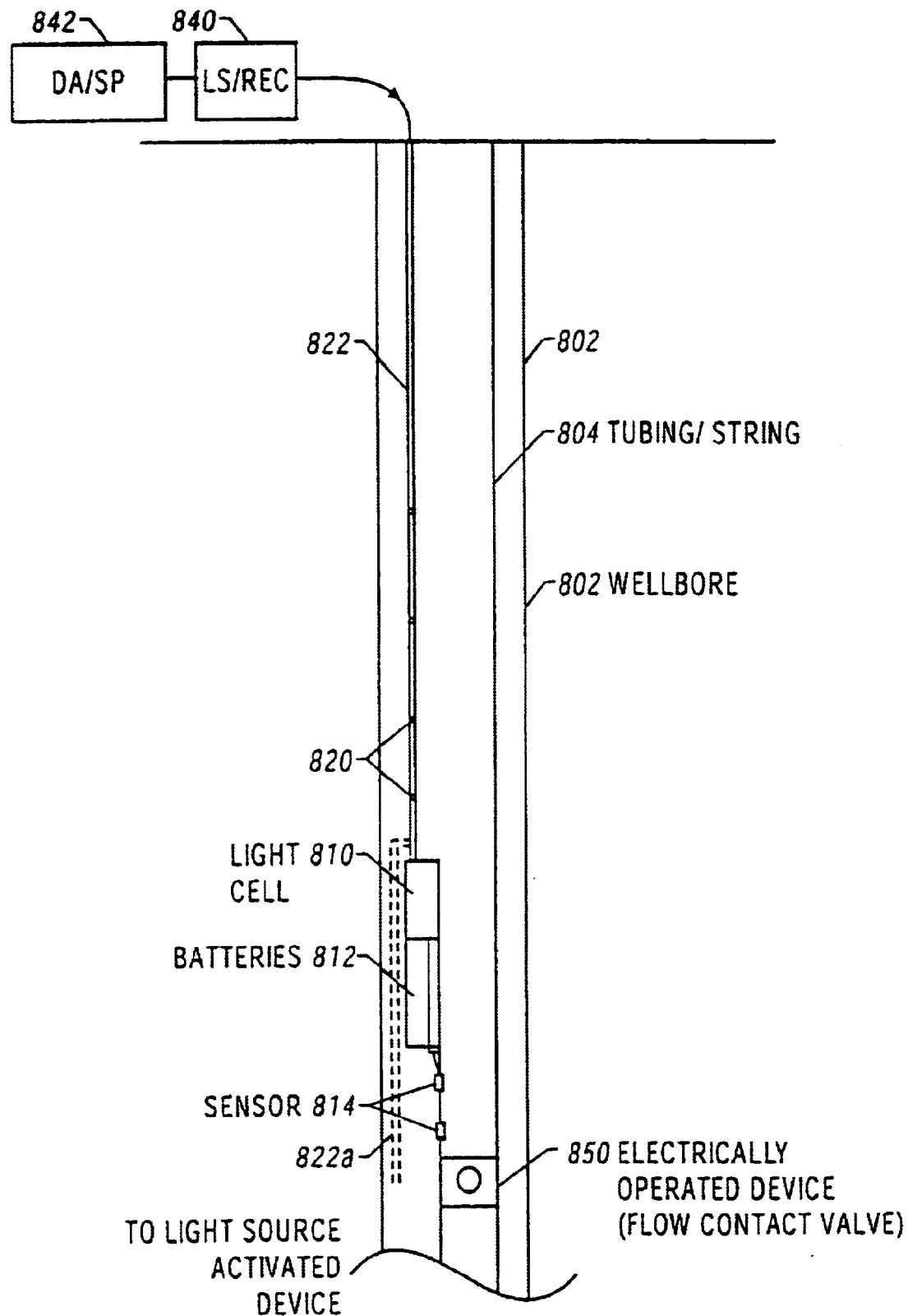
FIG. 14 is a schematic illustration of a wellbore system wherein electric power is generated downhole utilizing a light cell for use in operating sensors and devices downhole.

Another aspect of the invention is the ability to transmit optical energy downhole and convert it to another form of energy suitable for operation of downhole devices FIG. 14 shows a wellbore 802 with a production string 804 having one or more electrically-operated or optically-operated deices, generally denoted herein by numeral 850 and one or more downhole sensors 814. The string 804 includes batteries 812 which provide electrical power to the devices 850 and sensors 814. The batteries are charged by generating power downhole by turbines (not shown) or by supplying power for the surface via a cable (not shown).

In the present invention a light cell 810 is provided in the string 804 which is coupled to an optical fiber 822 that has one or more sensors 820 associated therewith. A light source 840 at the surface provides light to the light cell 810 which generates electricity which charges the downhill batteries 812. The light cell 810 essentially trickle changes the batteries. In many applications the downhole devices, such as devices 850, are activated infrequently. Trickle charging the batteries may be sufficient and thus may eliminate the use of other power generation devices. In applications ring greater power consumption, the light cell may be used in conjunction with other power generator devices.

Alternatively, if the device 850 is optically-activated the fiber 822 is coupled to the device 850 as shown by the dotted line 822a and is activated by supplying optical pulses from the surface unit 810. Thus in the configuration of FIG. 14, a fiber optics device is utilized to generate electrical energy downhole, which is then used to charge a source, such as a battery, or operate a device. The fiber 822 is also used to provide two-way communication between the DA/SP 842 and downhole sensors and devices.

Figure 15C:
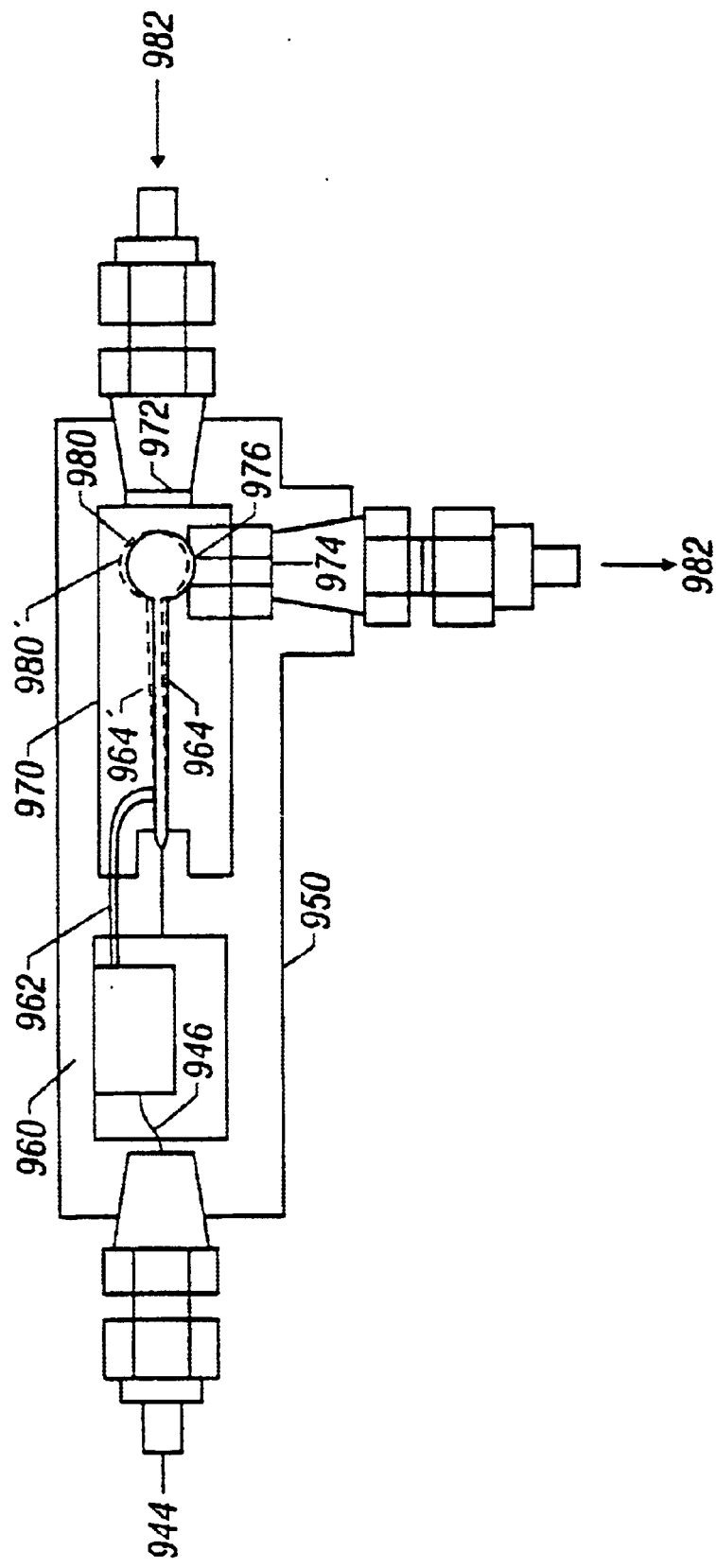

FIG. 15 is a schematic illustration of a wellbore system 900 utilizing the fiber optic energy producing devices according one embodiment of the present invention. System 900 includes a wellbore 902 having a surface casing 901 installed a relatively short depth 904a from the surface 904. After the wellbore 902 has been drilled to a desired depth, a completion or production string 906 is conveyed into the wellbore 902. A fiber optic energy generation device 920 place in the string 906 generates mechanical energy. The operation of the fiber optic device 920 is described in reference to FIGS. 15A–15C.

The fiber optic device 920A shown in FIG. 15A contains a sealed chamber 922a containing a gas 923 which will expand rapidly when optical energy such as laser energy is applied to the gas 923. A piston 924a disposed in the device 920A moves outward when the gas 923 expands. When the optical energy is not bang applied to the gas 923; a spring 926a or another suitable device coupled to a piston rod 925a forces the piston 926a back to its original position. The gas 923 is periodically charged with the optical energy conveyed to the device 920a via an optical conductor or fiber 944. FIG. 15B shows the optical device 920B wherein a spring 926b is disposed within the enclosure 921 to urge the piston 924b back to its original position.

Referring back to FIG. 15, the outward motion of the member 925 of the device 920 cases a valve 930 to open allowing the wellbore fluid 908 at the hydrostatic pressure to enter through port 932. The valve 930 is coupled to hydraulically-operated device 935 in a manner that allows the fluid 908 under pressure to enter the device 935 via the port 932. Thus, in the configuration of FIG. 15, fiber optic device 920 controls the flow of the fluid 908 at the hydrostatic pressure to the hydraulically-operated device 935. The device 935 may be a packer, fluid valve, safety valve, perforating device, anchor, sliding sleeve etc. The operation of the device 920 is preferably controlled from the surface 904, a light source LS 940 provides the optical energy to the device 908 via the fiber 944. One or more sensors 927 may be provided to obtain feedback relating to the downhole operations. The sensors 927 provide measurements relating to the fluid flow, force applied to the valve 930, downhole pressures, downhole temperatures etc. The signals from sensors 927 may be processed downhole or sent to the surface data acquisition and processing unit 942 via the fiber 944.

An alternate embodiment of a light actuated transducer for use in fluid flow control is shown in FIG. 15C. The device 950 includes a photovoltaic cell 960 and a bi-morph element fluid valve cell 970. Optical energy from an optical fiber 944 is connected by means of optical lead 946 to a photovoltaic cell 960. The photovoltaic cell 960 upon excitation by light produces an electric current that is conveyed by lead 962 to a bimetallic strip (bi-morph element) 964. Passage of current through the bimetallic strip causes it to bend to position 964' and move a ball 980 that rests in a valve seat 976. Motion of the ball 980 away from the seat to 980' enables a fluid 982 to flow through the inlet port 972 in the bi-morph element fluid valve cell 970 and the outlet port 974. Other arrangements of the bimetallic strip and the valve arrangement would be familiar to those versed in the art. This illustrates equipment in which optical energy is converted first to electrical energy and then to mechanical motion.

In yet another embodiment of the invention (not shown), the optical energy is used to alter the physical properties of a photosensitive material, such as a gel, that is incorporated in a flow control device. Screens having a gravel pack are commonly used in oil and gas production to screen out particulate matter. In one embodiment of the invention, a photosensitive gel is used as the packing material in the screen. Activation of the gel by optical energy changes the physical characteristics of the gel, partially crystallizing it. This makes it possible to adjust the size of particles flowing through the screen.

Figure 16:
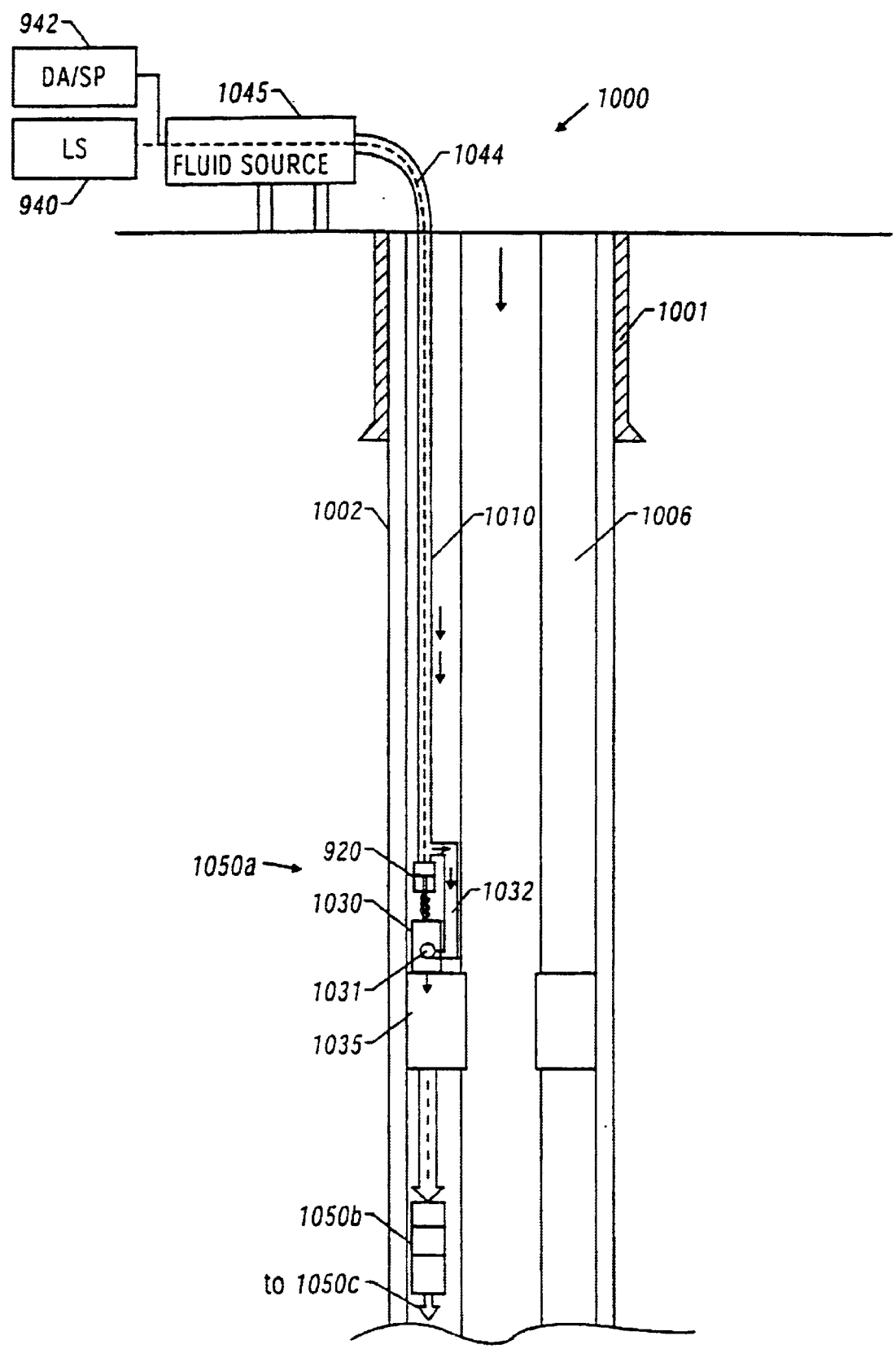
FIG. 16 is a schematic illustration of a wellbore with a completion string having a fiber optic energy generation device for operating a series of devices downhole.

FIG. 16 shows a wellbore system 1000 wherein the fiber optic devices 1020 are used to operate one or more downhole devices and wherein the pressurized fluid is supplied through a conduit which also carries the optical fiber to the devices 1020 from the surface 904. A valve 1030 is operated by the optic device 920 in the manner described above with reference to FIG. 15. Pressurized fluid 1032 from a source 1045 is supplied to the valve 1030 via a conduit 1010. The conduit 1010 the optical fiber 1044 is pumped through the conduit from an the surface. Alternatively, the conduit 1010 containing the fiber 1044 may be assembled at the surface and deployed into the wellbore with the string 1006. To operate the device 1035, the fiber optic device 920 is operated and the fluid 1032 under pressure is continuously supplied to the valve 1030 via the conduit 1010, which activates or sets the device 1035. Other downhole devices 1050b, 1050c etc. may be disposed in the string 1006 or in the wellbore 1002. Each such device utilizes separate fiber optic devices 920 and may utilize a common conduit 1010 for the optical fiber 1044 and/or for the pressurized fluid 1032.

Figure 17A:
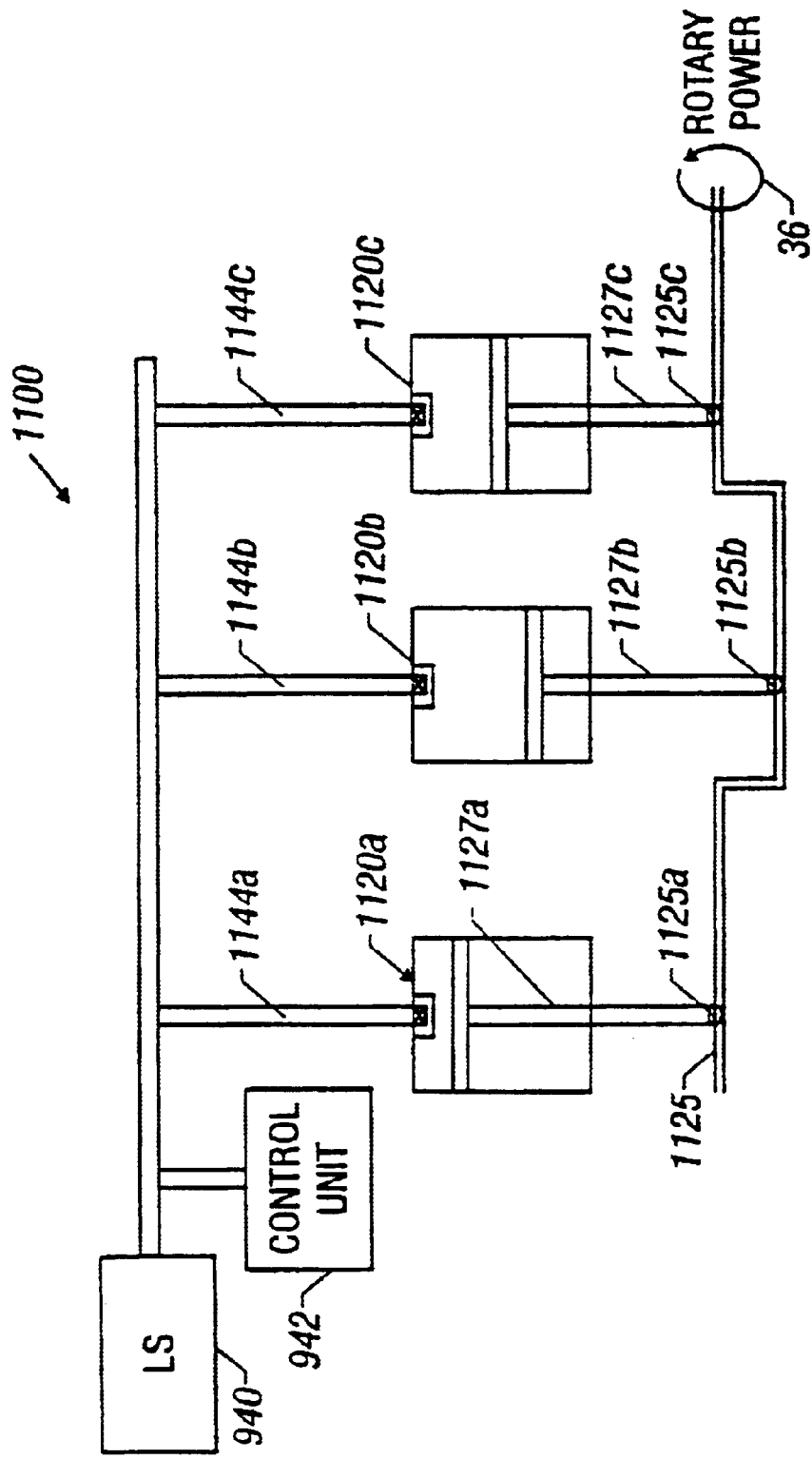
FIGS. 17A–17C show certain configurations for utilizing the fiber optic devices to produce the desired energy.

FIG. 17A shown a configuration utilizing multiple fiber optic devices 1120a–1120c to generate rotary power. The devices 1120a–1120c are similar to the devices 920 described above. Light energy is preferably provided to such devices via a common optical fiber 1144. The source 940 operates the devices 1120a–1120c in a particular order with a predetermined phase difference. An address system (not shown) may be utilized to address the devices by signals generated for such devices. The piston arms 1127a–1127c are coupled to a cam 1125 at locations 1125a–1125c respectively, which rotates in the direction 1136 to provide rotary power. The rotary power may be utilized for any denied purpose, such as to operate a pump or a generator to generate electrical power.

Figure 17C:
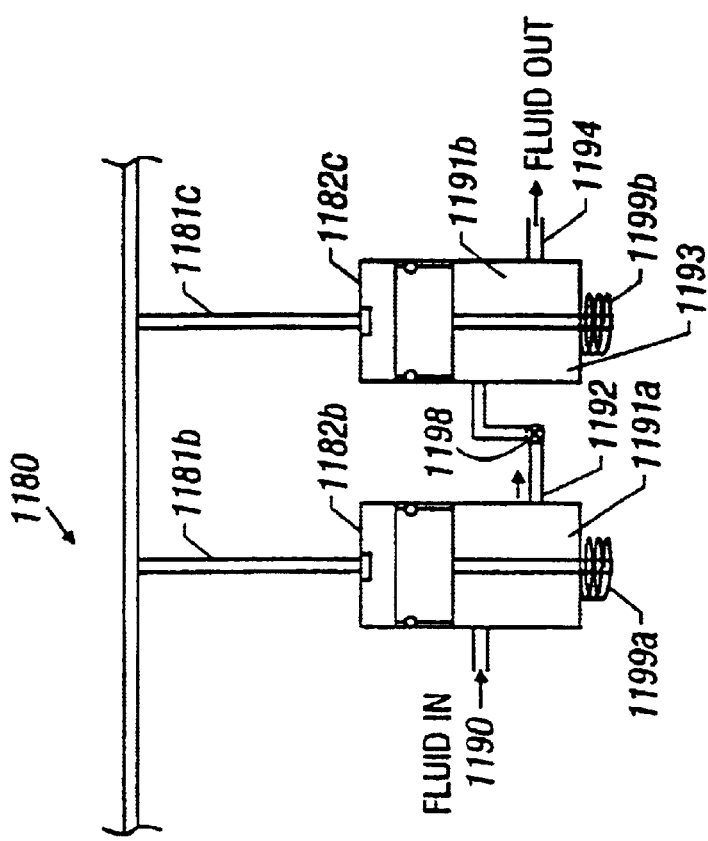
Figure 17B:
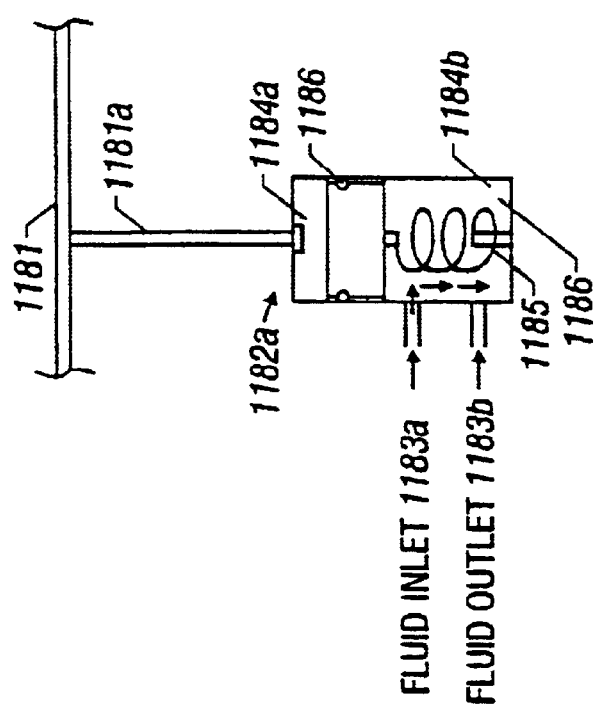

FIGS. 17B–17C shows a configuration wherein the fiber optic devices are used to pump fluids. The fiber optic devices 1182a of FIG. 17B contains a firing cylinder 1184a and a second cylinder 1184b. The send or hydraulic cylinder contains an outlet port 1183b. Suitable fluid is supplied to the hydraulic cylinder via the inlet port 1183a. When the device 1182a is fired, the piston 1186 moves downward, blocking the inlet port 1183a and simultaneously displacing the fluid 1186 from the cylinder 1184b via the outlet port 1183b. The spring 1185 forces the piston 1186 to return to its original position, uncovering the inlet port, until the next firing of the device 1182a. In this manner the device 1182a may be utilized to pump fluid. The flow rate is controlled by the firing frequency and the size of the fluid chamber 1184b.

FIG. 17C shows two fiber optic devices 382b and 382c (similar to the device 382a) connected in series to pump a fluid. In this configuration, when the device 382b is fired, fluid 390 from the channels 391 of the device 382 discharges into the chamber 391b of the device 382c via line 392. A one-way check valve allows the fluid to flow only in the direction of the device 382c. The firing of the device 382c discharges the fluid from the chamber 391b via line 394 to the next stage.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of controlling production from a wellbore, comprising:
   (a) providing a producing string carrying an electrical submersible pump for pumping wellbore fluid to the surface, said string carrying a power supply line from a surface location to the pump for providing electrical power to the pump; and
   (b) providing an optical fiber carrying at least one fiber optic sensor along the power supply line for taking measurements of a wellbore parameter.

2. The method of claim 1 wherein at least one fiber optic sensor is placed below the pump.

3. The method of claim 2, wherein the sensor below the pump is selected from a group consisting of a (a) pressure sensor, (b) temperature sensor, (c) vibration sensor, and (d) flow measurement sensor.

4. The method of claim 1 further comprising controlling the operation of the electrical submersible pump in response to the wellbore parameter.

5. The method of claim 4 wherein the wellbore parameter is at least one of (a) temperature of the pump, (b) vibration of the pump, and (c) fluid flow by the pump.

6. The method of claim 1, further comprising using the at least one fiber optic sensor to measure vibration of the electrical submersible pump and a wellbore temperature.

7. The method of claim 6, further comprising adjusting a speed of the electrical submersible pump based on the measured vibration of the electrical submersible pump and the wellbore temperature.

8. The method of claim 1, further comprising monitoring a health of the electrical submersible pump based at least in part on the wellbore parameter.

9. An apparatus for use in a wellbore, comprising:
   (a) a conduit for extending into the wellbore;
   (b) an electric powerline in the conduit carrying electric power to a location in the wellbore; and
   (c) a plurality of fiber optic sensors distributed along and adjacent the electric powerline, said fiber optic sensors providing measurements representing a physical condition of the electric powerline.

10. A system for controlling a downhole device in a wellbore comprising:
   (a) a fiber optic sensor in the wellbore to provide measurements for a downhole parameter;
   (b) a source of power for supplying power to operate the downhole device; and
   (c) a controller to provide signals to adjust operation of the downhole device responsive to the fiber optic sensor measurements.

11. A system for use in a wellbore, comprising:
   a string having a pump for pumping fluid in the wellbore, the string further having a power supply line from a surface location to the pump for providing electrical power to the pump; and
   at least one fiber optic sensor along the power supply line to take measurements of one or more downhole parameters.

12. The system of claim 11, wherein the at least one fiber optic sensor is placed below the pump.

13. The system of claim 11, wherein the fiber optic sensor is selected from a group consisting of a fiber optic sensor to measure pressure, a fiber optic sensor to measure temperature, a fiber optic sensor to measure vibration, and a fiber optic sensor to measure flow rate.

14. The system of claim 11, further comprising a controller to control the operation of the pump in response to measurements of the one or more downhole parameters.

* * * * *